US012674139B2

(12) United States Patent
Yamazaki et al.

(10) Patent No.: US 12,674,139 B2
(45) Date of Patent: Jul. 7, 2026

(54) SERUM-FREE MEDIUM NOT CONTAINING ALBUMIN AND SUITED FOR CULTURING HUMAN HEMATOPOIETIC STEM CELLS, AND ALBUMIN-FREE CULTURING METHOD

(71) Applicant: The University of Tokyo, Tokyo (JP)

(72) Inventors: Satoshi Yamazaki, Tokyo (JP); Motoo Watanabe, Tokyo (JP); Masatoshi Sakurai, Tokyo (JP); Hiromitsu Nakauchi, Tokyo (JP)

(73) Assignee: The University of Tokyo, Tokyo (JP)

( * ) Notice: Subject to any disclaimer, the term of this patent is extended or adjusted under 35 U.S.C. 154(b) by 1078 days.

(21) Appl. No.: 17/641,699

(22) PCT Filed: Sep. 11, 2020

(86) PCT No.: PCT/JP2020/034470
§ 371 (c)(1),
(2) Date: Mar. 9, 2022

(87) PCT Pub. No.: WO2021/049617
PCT Pub. Date: Mar. 18, 2021

(65) Prior Publication Data
US 2022/0298479 A1 Sep. 22, 2022

(30) Foreign Application Priority Data
Sep. 11, 2019 (JP) ................................. 2019-165470

(51) Int. Cl.
*C12N 5/0789* (2010.01)

(52) U.S. Cl.
CPC ........ *C12N 5/0647* (2013.01); *C12N 2500/50* (2013.01); *C12N 2500/90* (2013.01); *C12N 2501/125* (2013.01); *C12N 2501/145* (2013.01)

(58) Field of Classification Search
CPC .............. C12N 5/0647; C12N 2500/50; C12N 2500/90; C12N 2501/125; C12N 2501/145
See application file for complete search history.

(56) References Cited

U.S. PATENT DOCUMENTS

2023/0106769 A1 4/2023 Yamazaki et al.

FOREIGN PATENT DOCUMENTS

| CN | 105713880 A | 6/2016 |
| JP | 2014-176353 A | 9/2014 |
| WO | WO-2006/045064 A2 | 4/2006 |
| WO | WO-2014/110020 A1 | 7/2014 |
| WO | WO-2021/149799 A1 | 7/2021 |

OTHER PUBLICATIONS

Kumar et al. "The combined influence of substrate elasticity and surface-grafted molecules on the ex vivo expansion of hematopoietic stem and progenitor cells." Biomaterials 34.31 (2013): 7632-7644 (Year: 2013).*
Wilkinson et al. "Long-term ex vivo haematopoietic-stem-cell expansion allows nonconditioned transplantation." Nature 571.7763 (Jul. 2019): 117-121. (Year: 2019).*
Lennartsson et al. "Stem cell factor receptor/c-Kit: from basic science to clinical implications." Physiological reviews 92.4 (2012): 1619-1649. (Year: 2012).*
Kazuo (JP 2014/176353 A) (EPO machine translation) (Year: 2014).*
Nishino et al. "Ex vivo expansion of human hematopoietic stem cells by a small-molecule agonist of c-MPL." Experimental hematology 37.11 (2009): 1364-1377. (Year: 2009).*
Kuter, David J. "New thrombopoietic growth factors." Clinical Lymphoma and Myeloma 9 (2009): S347-S356. (Year: 2009).*
Ieyasu et al., "An All-Recombinant Protein-Based Culture System Specifically Identifies Hematopoietic Stem Cell Maintenance Factors," Stem Cell Reports, Mar. 14, 2017, 8:500-508.
International Search Report dated Nov. 10, 2020 in PCT/JP2020/034470, with English translation.
Wang et al., "Hepatic Parenchymal Changes following Transcatheter Embolization and Chemoembolization in a Rabbit Tumor Model," PLoS One, Aug. 13, 2013, 8(8):e70757, 1-7.
Wilkinson et al., "Long-term ex vivo haematopoietic-stem-cell expansion allows nonconditioned transplantation," Nature, Jul. 4, 2019, 571:117-121.
Fares et al., "Cord blood expansion. Pyrimidoindole derivatives are agonists of human hematopoietic stem cell self-renewal," Science, Sep. 19, 2014, 345(6203):1509-1512.
Office Action dated Jul. 31, 2024 in CA 3150657.
Nishino et al., "Ex vivo expansion of human hematopoietic stem cells by a small-molecule agonist of c-MPL," Experimental Hematology, 2009, 37(11):1364-1377.
Office Action dated Aug. 22, 2023 in CN 202080077183.0, with English translation.
Feng et al., "Synthesis and evaluation of pyrimidoindole analogs in umbilical cord blood ex vivo expansion," European Journal of Medicinal Chemistry, 2019, 174:181-197.
Ikeda et al., "Development of thrombopoietin receptor agonists for clinical use," Journal of Thrombosis and Haemostasis, 2009, 7(Suppl. 1): 239-244.
Nogami et al., "The effect of a novel, small non-peptidyl molecule butyzamide on human thrombopoietin receptor and megakaryopoiesis," haematologica, 2008, 93(10):1495-1504.
Office Action dated Sep. 17, 2024 in JP 2021-545616, with English translation.
Office Action dated Mar. 30, 2023 in CA 3,150,657.

(Continued)

*Primary Examiner* — Emily A Cordas

(74) *Attorney, Agent, or Firm* — KDW Firm PLLC

(57) ABSTRACT

The present invention discloses a composition of an albumin-free, serum-free medium suited for culturing human hematopoietic stem cells and an albumin-free culturing method. According to the present invention, a method of culturing human hematopoietic stem cells is provided which comprises bringing human hematopoietic stem cells into contact with PVA and a PI3K activator.

13 Claims, 13 Drawing Sheets

(56)             References Cited

OTHER PUBLICATIONS

Xiao, X et al., "Targeting JNK pathway promotes human hematopoietic stem cell expansion," Cell Discovery, Jan. 8, 2019, 5(2):1-12, [online] https://www.nature.com/articles/s41421-018-0072-8.

Supplementary European Search Report dated Aug. 14, 2023 in EP 20863479.0.

Supplementary European Search Report dated Aug. 14, 2023 in EP 20863479.

Wilkinson et al., "Ex vivo mouse hematopoietic stem cell expansion using polyvinyl alcohol," Research Square, Apr. 19, 2019, 1-9, URL: chrome-extension://efaidnbmnnnibpcajpcglclefindmkaj/https://assets.researchsquare.com/files/pex-173/vl/e848edf9-e818-47fa-9829-lc21f3aaf7e7.pdf?c=1631825623 [retrieved on Jul. 31, 2023].

\* cited by examiner

Number of all cells                    Number of CD34+ cells

PI3K activator + TPOago

SERUM-FREE MEDIUM NOT CONTAINING ALBUMIN AND SUITED FOR CULTURING HUMAN HEMATOPOIETIC STEM CELLS, AND ALBUMIN-FREE CULTURING METHOD

CROSS-REFERENCE TO RELATED APPLICATIONS

This application is the U.S. National Stage of PCT/JP2020/034470, filed Sep. 11, 2020, which claims priority to JP 2019-165470, filed Sep. 11, 2019.

TECHNICAL FIELD

The present invention discloses a composition of an albumin-free, serum-free medium suited for culturing human hematopoietic stem cells and an albumin-free culturing method. According to the present invention, a method of culturing human hematopoietic stem cells is provided which comprises bringing human hematopoietic stem cells into contact with PVA and a PI3K activator.

BACKGROUND ART

Research has been under way on proliferation of hematopoietic stem cells in culture using a chemically defined medium, and it has been shown that mouse hematopoietic stem cells can be cultured using a chemically defined medium (Non-patent Literature 1).

CITATION LIST

Non-Patent Literature

Non-patent Literature 1: Wilkinson et al., Nature, 571: 117-121, 2019

SUMMARY OF INVENTION

The present invention provides a composition of an albumin-free, serum-free medium suited for culturing human hematopoietic stem cells and an albumin-free culturing method.

The present inventors found and reported that addition of polyvinyl alcohol (PVA) to a serum-free medium not comprising albumin enabled long-term, large-scale proliferation of mouse hematopoietic stem cells (may also be referred to as "KSL cells," which is derived from the method of isolating these cells) (Wilkinson et al., Nature, 571:117-121, 2019). However, a method of proliferating human hematopoietic stem cells in a serum-free medium not comprising albumin has not been established. The present inventors have now found that various signaling pathways including the PI3K pathway and the Akt pathway are weakly activated in human hematopoietic stem cells in the presence of PVA, tissue factor (i.e., SCF), and thrombopoietin (TPO) in a serum-free medium not comprising albumin. The present inventors have also found that human hematopoietic stem cells proliferate in the presence of PVA, SCF, and TPO in a serum-free medium not comprising albumin by adding a PI3K activator. The present inventors have further found that a PI3K activator can completely replace SCF in the presence of PVA in a serum-free medium not comprising albumin. The present inventors have even further found that TPO can be replaced with a TPO receptor agonist in the presence of PVA and a PI3K activator in a serum-free medium not comprising albumin. The present inventors have even further found that long-term culture of human hematopoietic stem cells in the presence of PVA, a PI3K activator, and TPO or a TPO receptor agonist in a serum-free medium not comprising albumin promotes differentiation of the cells into megakaryocytic lineage cells. The present inventors have even further found that addition of UM171 to the medium inhibits differentiation into megakaryocytic lineage cells or reduces the number of megakaryocytic lineage cells, and that UM171 is useful to maintain and proliferate human hematopoietic stem cells which are $CD34^+$ cells.

According to the present invention, the following inventions are provided:

[1]
A method of culturing human hematopoietic stem cells, the method comprising culturing human hematopoietic stem cells in a culture medium,
the culture medium comprising polyvinyl alcohol, not comprising albumin, and
(1) comprising a phosphatidylinositol 3-kinase (PI3K) activator and one or more selected from the group consisting of thrombopoietin (TPO) and TPO receptor agonists;
(2) comprising one or more selected from the group consisting of a stem cell factor (SCF) and PI3K activators and a TPO receptor agonist; or
(3) comprising a PI3K activator and a TPO receptor agonist,
wherein the number of human hematopoietic stem cells is increased by the culture.

[2]
The method according to [1], which comprises obtaining an increased amount of human hematopoietic stem cells.

[3]
The method according to [1] or [2], wherein the culture medium comprises a PI3K activator and does not comprise a stem cell factor (SCF).

[4]
The method according to any of [1] to [3], wherein the culture medium comprises a PI3K activator and a TPO agonist.

[5]
The method according to [4], wherein the culture medium comprises neither SCF nor TPO.

[6]
The method according to any of [1] to [5], wherein the culture medium further comprises 4-N-[2-benzyl-7-(2-methyltetrazol-5-yl)-9H-pyrimido[4,5-b]indol-4-yl]cyclohexane-1,4-diamine (UM171).

[7]
The method according to [6], wherein the duration of culture is 7 days or longer.

[8]
A composition not comprising albumin,
the composition comprising human hematopoietic stem cells, polyvinyl alcohol, and
(1) a PI3K activator and one or more selected from the group consisting of TPO and TPO receptor agonists;
(2) one or more selected from the group consisting of SCF and PI3K activators, and a TPO receptor agonist; or
(3) a PI3K activator and a TPO receptor agonist.

[9]
The composition according to [8], which comprises a PI3K activator and a TPO receptor agonist.

3                                                                                                4

[10]

The composition according to [8] or [9], which further comprises 4-N-[2-benzyl-7-(2-methyltetrazol-5-yl)-9H-pyrimido[4,5-b]indol-4-yl]cyclohexane-1,4-diamine (UM171).

[11]

A human hematopoietic stem cell obtained by the method according to any of [1] to [7].

[12]

A culture medium for human hematopoietic stem cells, comprising polyvinyl alcohol, not comprising albumin, and
    (1) comprising a PI3K activator and one or more selected from the group consisting of TPO and TPO receptor agonists;
    (2) comprising one or more selected from the group consisting of SCF and PI3K activators and a TPO receptor agonist; or
    (3) comprising a PI3K activator and a TPO receptor agonist.

[1]

A method of culturing or manufacturing human hematopoietic stem cells,
    the method comprising culturing human hematopoietic stem cells in a culture medium,
    the culture medium comprising polyvinyl alcohol and
    (1) comprising a phosphatidylinositol 3-kinase (PI3K) activator and one or more selected from the group consisting of thrombopoietin (TPO) and TPO receptor agonists;
    (2) comprising one or more selected from the group consisting of stem cell factor (SCF) and PI3K activators, and a TPO receptor agonist; or
    (3) comprising a PI3K activator and a TPO receptor agonist,
    wherein the number of human hematopoietic stem cells is increased by the culture.

[2]

The method according to [1], wherein the culture medium is a serum-free medium.

[3]

The method according to [1], wherein the culture medium is a chemically defined medium.

[4]

The method according to any of [1] to [3], wherein the culture medium comprises substantially no albumin.

[5]

The method according to any of [1] to [4], which comprises obtaining an increased amount of human hematopoietic stem cells.

[6]

The method according to any of [1] to [5], wherein the culture medium comprises a PI3K activator and does not comprise the stem cell factor (SCF).

[7]

The method according to any of [1] to [6], wherein the culture medium comprises a PI3K activator and a TPO agonist.

[8]

The method according to [7], wherein the culture medium comprises neither SCF nor TPO.

[9]

The method according to any of [1] to [8], wherein the culture medium further comprises 4-N-[2-benzyl-7-(2-methyltetrazol-5-yl)-9H-pyrimido[4,5-b]indol-4-yl]cyclohexane-1,4-diamine (UM171).

[10]

The method according to [9], wherein the duration of culture is 7 days or longer.

[11]

A composition comprising human hematopoietic stem cells, polyvinyl alcohol as an albumin replacement, and
    (1) a PI3K activator and one or more selected from the group consisting of TPO and TPO receptor agonists;
    (2) one or more selected from the group consisting of SCF and PI3K activators, and a TPO receptor agonist; or
    (3) a PI3K activator and a TPO receptor agonist.

[12]

The composition according to [11], which comprises a PI3K activator and a TPO receptor agonist.

[13]

The composition according to [11] or [12], which further comprises 4-N-[2-benzyl-7-(2-methyltetrazol-5-yl)-9H-pyrimido[4,5-b]indol-4-yl]cyclohexane-1,4-diamine (UM171).

[14]

A human hematopoietic stem cell obtained by the method according to any of [1] to [10].

[15]

A culture medium for human hematopoietic stem cells comprising polyvinyl alcohol as an albumin replacement and
    (1) comprising a PI3K activator and one or more selected from the group consisting of TPO and TPO receptor agonists;
    (2) comprising one or more selected from the group consisting of SCF and PI3K activators, and a TPO receptor agonist; or
    (3) comprising a PI3K activator and a TPO receptor agonist.

[16]

The culture medium according to [15], which is a serum-free medium.

[17]

The medium according to [15], which is a chemically defined medium.

[18]

The medium according to any of [15] to [17], which does not comprise albumin.

BRIEF DESCRIPTION OF DRAWINGS

FIG. 4 shows that comparison between the conditions with SCF and without SCF revealed no statistically significant difference between the conditions in the number of total cells or the number of CD34$^+$ cells at day 7 of culture.

DETAILED DESCRIPTION OF THE INVENTION

Figure 1:
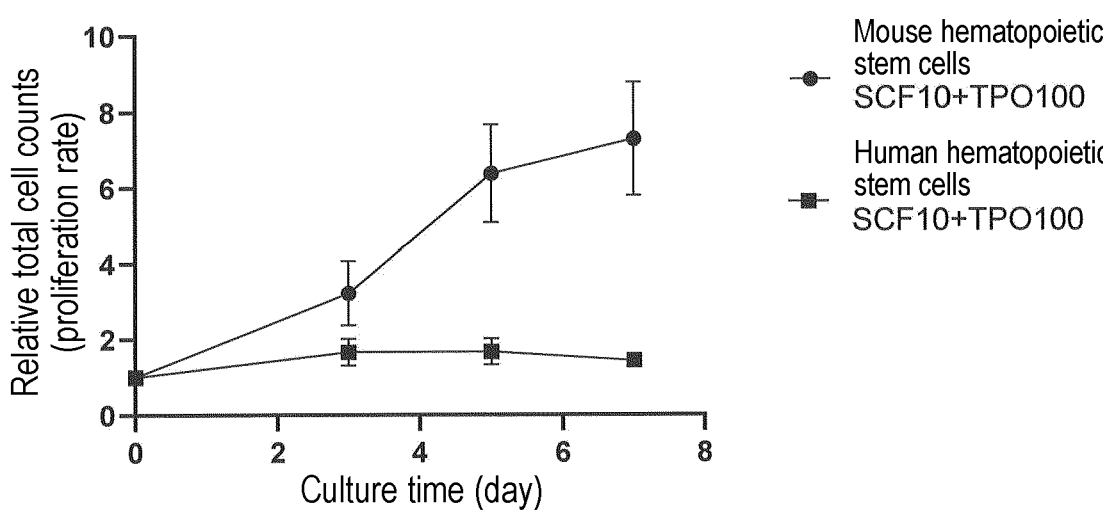
FIG. 1 shows the results of culturing mouse hematopoietic stem cells (mouse KSL cells) and human hematopoietic stem cells (CD34$^+$CD38$^-$ cells) in the presence of 10 ng/mL tissue factor (i.e., SCF) and 100 ng/mL thrombopoietin (TPO), derived from a mouse and a human, respectively, in an albumin-free, serum-free medium comprising polyvinyl alcohol (PVA).

In the present specification, "hematopoietic stem cells" are stem cells that can be differentiated into blood cells. Hematopoietic stem cells can be collected from bone marrow, umbilical cord, placenta, and peripheral blood. Human hematopoietic stem cells are CD34-positive cells. In humans, hematopoietic stem cells are known to be abundant in CD34-positive, CD38-negative cell fractions. Therefore, human hematopoietic stem cells can be CD34 positive and CD38 negative. Hematopoietic stem cells may be cells obtained by ex vivo differentiation of multipotent stem cells such as ES cells and iPS cells.

In the present specification, the term "ex vivo" means outside of an organism. In the present specification, ex vivo is used in contrast to in vivo (in an organism) and means the state in which cells existing in a living body have been removed from the inside of the living body to the outside of the living body. Culture can be performed ex vivo.

In the present specification, the term "positive" means that cells are expressing a molecule identified with a term occurring immediately before the term. In the present specification, "positive" may be simply expressed as "+."

In the present specification, the term "polyvinyl alcohol" means a vinyl alcohol polymer. Polyvinyl alcohol can be obtained by saponifying polyvinyl acetate obtained by polymerizing vinyl acetate monomers. The weight average molecular weight ($M_W$) of polyvinyl alcohol can be, for example, 1 kDa to 20 kDa, 3 kDa to 17 kDa, 5 kDa to 15 kDa, or 7 kDa to 13 kDa. When PVA is obtained by saponifying polyvinyl acetate by the above-mentioned method, the saponification rate can be 80% or higher, 85% or higher, 90% or higher, 95% or higher, or 99% or higher.

In the present specification, "albumin" is a protein known as a component of plasma. Albumin is said to account for 60% of plasma proteins and is abundant in blood, serum, and plasma. Albumin is thought to play a role of maintaining osmotic pressure of blood in a living body and bind to and transport biological substances such as fatty acid and hormones. The importance of serum albumin in maintenance culture of hematopoietic stem cells is also known. Human serum albumin (hereinafter, may be referred to as "HSA") is serum albumin of humans and can be, for example, a protein having an amino acid sequence registered with GenBank accession number: AAN17825.1 or human serum albumin having an amino acid sequence corresponding thereto.

In the present specification, the expression "comprising B as a replacement of A" means comprising B instead of A. Comprising B instead of A means that A is partially or completely replaced with B. The expression "comprising B as a replacement of A" can mean comprising B while comprising substantially no A. "Comprising substantially no" permits contamination in an amount that cannot be prevented and an amount below the detection limit in a system. "Comprising substantially no" can also mean not permitting such contamination that can be prevented.

In the present specification, the term "agonist" refers to a substance that activates proteins such as receptors and enzymes.

In the present specification, "PI3K" means phosphatidylinositol 3-kinase. PI3K is an enzyme that phosphorylates inositol phospholipid, a cell component. Phosphatidylinositol 3,4,5-triphosphate (PIPS), which is produced by phosphorylation, phosphorylates Akt (also known as protein kinase B), and transmits a signal thereof to the downstream. In the present specification, the term "PI3K activator" means a receptor tyrosine kinase agonist or a substance that activates PI3K.

In the present specification, "TPO" means thrombopoietin. TPO is a protein that is responsible for differentiation of hematopoietic stem cells into megakaryocytes. TPO is known to be involved in formal maintenance of hematopoietic stem cells. Human thrombopoietin can be, for example, a protein having an amino acid sequence registered with GenBank accession number: AAB33390.1 or thrombopoietin having an amino acid sequence corresponding thereto. TPO can encompass functional homologues of TPO and proteins having an amino acid sequence having 90% or higher, 95% or higher, or 100% identity to an amino acid sequence registered with GenBank accession number: AAB33390.1, and having functions of TPO.

In the present specification, the term "TPO receptor agonist" means a substance that is not TPO and activates a TPO receptor. Examples of a TPO receptor agonist include variants of TPO other than TPO, peptides, and compounds that activate a TPO receptor. In the present specification, "compound" is a concept encompassing organic compounds.

In the present specification, stem cell factor (SCF) is a hematopoietic cell growth factor that acts at an early stage of the hematopoietic function. Human stem cell factor can be, for example, a protein having an amino acid sequence registered with GenBank accession number:AAA85450.1 or SCF having an amino acid sequence corresponding thereto. SCF can encompass functional homologues of SCF and proteins having an amino acid sequence having 90% or higher, 95% or higher, or 100% identity to an amino acid sequence registered with GenBank accession number: AAB33390.1 and having functions of SCF.

In the present specification, the term "to culture" means to incubate cells under a condition suited for proliferation or maintenance of the cells. Incubation can be performed preferably at 37° C. in a 5% $CO_2$ atmosphere for human cells. When "culture" is associated with proliferation, "culture" is understood as production of proliferated cells. In the present specification, "culture" can be performed in a serum-free medium. In the present specification, "culture" can be performed in a chemically defined culture medium (or in a completely synthetic medium). A chemically defined culture medium is a serum-free medium.

In the present specification, the term "culture medium" means a medium used to culture cells. A culture medium can be prepared by adding required components to a base medium. The required components can be a pH modifier, a sugar source, such as glucose, an antibiotic (e.g., penicillin and streptomycin), and essential amino acids, such as glutamine, as well as culture additives such as insulin, transferrin, selenium (e.g., sodium selenite), and ethanolamine. A culture medium can be a liquid medium.

In the present specification, the term "cytotoxic" means a property of having an action of decreasing the number of cells or an action of killing cells during culture. In the present specification, the term "non-cytotoxic" refers to a property of not decreasing the number of cells by culture. Some substances can become cytotoxic when the concentration thereof is increased. In this case, however, a substance can be defined as being non-cytotoxic if expected beneficial effects of this substance can be exhibited when the concentration is decreased to such an extent that cytotoxicity does not occur.

The present inventors found and reported that addition of polyvinyl alcohol (PVA) to a serum-free medium not comprising albumin enabled long-term large-scale proliferation of mouse hematopoietic stem cells (may also be referred to KSL cells, which is derived from the method of isolating these cells) (Wilkinson et al., Nature, 571:117-121, 2019). However, a method of proliferating human hematopoietic stem cells in a serum-free medium not comprising albumin has not been established. The present inventors have now found that various signaling pathways including the PI3K pathway and the Akt pathway were weakly activated in human hematopoietic stem cells in the presence of PVA, SCF, and TPO in a serum-free medium not comprising albumin. The present inventors have also found that human hematopoietic stem cells proliferate in the presence of PVA, SCF, and TPO in a serum-free medium not comprising albumin by adding a PI3K activator. The present inventors have further found that a PI3K activator can completely replace SCF in the presence of PVA in a serum-free medium not comprising albumin. The present inventors have even further found that TPO can be replaced with a TPO receptor agonist in the presence of PVA and a PI3K activator in a serum-free medium not comprising albumin. The present inventors have even further found that long-term culture of human hematopoietic stem cells in the presence of PVA, a PI3K activator, and TPO or a TPO receptor agonist in a serum-free medium not comprising albumin promotes differentiation of the cells into megakaryocytic lineage cells. The present inventors have even further found that addition of UM171 to the medium inhibits differentiation into megakaryocytic lineage cells or reduces the number of megakaryocytic lineage cells, and that UM171 is useful to maintain and proliferate human hematopoietic stem cells which are CD34+ cells.

Thus, according to the present invention, a method of culturing human hematopoietic stem cells, the method comprising culturing human hematopoietic stem cells in a culture medium, the culture medium comprising polyvinyl alcohol, not comprising albumin, and (1) comprising a phosphatidylinositol 3-kinase (PI3K) activator and one or more selected from the group consisting of thrombopoietin (TPO) and TPO receptor agonists;

(2) comprising one or more selected from the group consisting of a stem cell factor (SCF) and PI3K activators, and a TPO receptor agonist; or (3) comprising a PI3K activator and a TPO receptor agonist, is provided. In this embodiment, the number of human hematopoietic stem cells can be increased or maintained by the above-mentioned culture.

According to the present invention, a method of culturing human hematopoietic stem cells in a culture medium, the method comprising bringing human hematopoietic stem cells into contact with polyvinyl alcohol in the culture medium, and comprising bringing human hematopoietic stem cells into (1) contact with a phosphatidylinositol 3-kinase (PI3K) activator and one or more selected from the group consisting of thrombopoietin (TPO) and TPO receptor agonists;

(2) contact with one or more selected from the group consisting of stem cell factor (SCF) and PI3K activators, and a TPO receptor agonist; or (3) contact with a PI3K activator and a TPO receptor agonist, in the culture medium is provided. In this embodiment, the number of human hematopoietic stem cells can be increased or maintained by the above-mentioned culture.

The present inventors have demonstrated that some compounds, including some TPO receptor agonists, can be cytotoxic against human hematopoietic stem cells in the absence of albumin and in the presence of PVA.

Thus, according to the present invention, a PI3K activator that is cytotoxic against human hematopoietic stem cells in the absence of albumin and in the presence of PVA is not used in the present invention. That is, a PI3K activator used in the present invention is non-cytotoxic.

Further, a TPO receptor agonist used in the present invention is non-cytotoxic against human hematopoietic stem cells in the absence of albumin and in the presence of PVA. Whether or not a PI3K activator is non-cytotoxic can be suitably examined by those skilled in the art by performing a culture assay of human hematopoietic stem cells. Here, a culture assay of human hematopoietic stem cells can be performed using an IMDM medium comprising 1% insulin-transferrin-selenium, 1% penicillin-streptomycin-glutamine, 100 ng/mL TPO, and 0.1% PVA. Whether or not a TPO receptor agonist is non-cytotoxic can also be examined by those skilled in the art by performing a culture assay of human hematopoietic stem cells. Here, a culture assay of human hematopoietic stem cells can be performed using an IMDM medium comprising 1% insulin-transferrin-selenium, 1% penicillin-streptomycin-glutamine, 10 ng/mL SCF, and 0.1% PVA.

In an embodiment of the present invention, a PI3K activator is a peptide represented by an amino acid sequence RQIKIWFQNRRMKWKKSDGGYMDMS and can be the peptide in which Y is phosphorylated (also referred to as "740Y-P").

In an embodiment of the present invention, a TPO receptor agonist can be 3-[4-[[[4-[2-methoxy-3-(1-tert-butyl-2-oxapentan-1-yl)phenyl]thiazol-2-yl]amino]carbonyl]-2,6-dichlorophenyl]-2-methylpropenoic acid (hereinafter, also referred to as "butyzamide").

In an embodiment of the present invention, a PI3K activator is 740Y-P, and a TPO receptor agonist is butyzamide.

In an embodiment of the present invention, a culture medium used in the culture method of the present invention is a serum-free medium. In an embodiment of the present invention, a culture medium used in the culture method of the present invention is a chemically defined medium. In an embodiment of the present invention, a culture medium used in the culture method of the present invention is a serum-free medium (preferably a chemically defined medium) comprising a PI3K activator and a TPO receptor agonist, wherein the PI3K activator is 740Y-P, and the TPO receptor agonist is butyzamide.

In an embodiment of the present invention, a culture medium used in the culture method of the present invention can be a culture medium for human hematopoietic stem cells, the culture medium comprising polyvinyl alcohol, not comprising albumin, and (1) comprising a PI3K activator and one or more selected from the group consisting of TPO and TPO receptor agonists;

(2) comprising one or more selected from the group consisting of SCF and PI3K activators and a TPO receptor agonist; or (3) comprising a PI3K activator and a TPO receptor agonist.

As a culture medium, a culture medium suited for culture of hematopoietic stem cells can be suitably used. Examples of a basal medium that can be used include S-clone™ SF-3 medium, F12 medium, StemSpan™ (StemCell Technologies Inc.), STEMa™ (STEM ALPHA), StemPro™-34 serum-free medium (Gibco Invitrogen), StemPro™ MSC serum-free medium (Invitrogen), StemMACSIM HSC-CFU medium (Miltenyi Biotech), S-Clone™ serum-free medium (SF-02, SF-03, CM-B, SF-B) (Sanko Junyaku Co., Ltd.), HPGM™ medium (Sanko Junyaku Co., Ltd.), AIM V™ medium (Invitrogen), Marrow MAXIM bone marrow medium (Invitrogen), KnockOut™ DMEM/F-12 medium (Invitrogen), Stemline® hematopoietic stem cell proliferation medium (Sigma), SYN serum-free medium (SYN H, SYN B) (AbCys SA), SPE-IV™ medium (AbCys SA), MyeloCult® medium (StemCell Technologies Inc.), HPG serum-free medium (Lonza), UltraCULTURE™ medium (Lonza), Opti-MEM™ medium (Gibco, Invitrogen, and others), MEM (Gibco, Invitrogen, and others), MEMα medium (Gibco, Invitrogen, and others), DMEM (Gibco, Invitrogen, and others), IMDM medium (Gibco, Invitrogen, and others), RPMI1640 medium (Gibco, Invitrogen, and others), Ham F-12 medium (Gibco and others), and RD medium. A culture medium comprises a basal medium. A culture medium may comprise one or more selected from, for example, insulin, apo-transferrin, sodium selenite, and ethanolamine, or all thereof. The culture medium may comprise HEPES, sodium pyruvate, vitamins, amino acids, heparin, heparan sulfate, chondroitin sulfate, and the like. A culture medium may comprise an antibiotic (e.g., penicillin and streptomycin). A culture medium may comprise glutamine. A culture medium may comprise, for example, insulin, apo-transferrin, sodium selenite, ethanolamine, and an antibiotic and may further comprise HEPES.

The culture medium of the present invention can comprise an effective amount of a non-cytotoxic PI3K activator and an effective amount of PVA to proliferate human hematopoietic stem cells in an environment in the absence of albumin and in the presence of PVA. The culture medium of the present invention may comprise either SCF or TPO or both thereof. The culture medium of the present invention may comprise an effective amount of non-cytotoxic TPO receptor agonist instead of TPO. The culture medium of the present invention may comprise an effective amount of a non-cytotoxic PI3K activator, an effective amount of PVA, an effective amount of either TPO or a non-cytotoxic TPO receptor agonist or both, and UM171.

According to the present invention, a method of culturing human hematopoietic stem cells can be a method for manufacturing megakaryocytic lineage cells from human hematopoietic stem cells. In this embodiment, a culture medium used in the culture method can be a culture medium comprising a PI3K activator and a TPO receptor agonist, wherein the PI3K activator is 740Y-P, and the TPO receptor agonist is butyzamide. In this specific embodiment, a culture medium can be free of UM171.

In an embodiment of the present invention, the culture method of the present invention can further comprise culturing in the presence of 4-N-[2-benzyl-7-(2-methyltetrazol-5-yl)-9H-pyrimido[4,5-b]indol-4-yl]cyclohexane-1,4-diamine (hereinafter, also referred to as "UM171"). In an embodiment of the present invention, a culture medium used in the culture method of the present invention can further comprise UM171. Consequently, human hematopoietic stem cells can easily maintain properties as human hematopoietic stem cells, or differentiation into megakaryocytic lineage cells (e.g., megakaryocytes precursor cells or megakaryocytes) can be inhibited.

In an embodiment of the present invention, the culture method of the present invention does not comprise culturing in the presence of 4-N-[2-benzyl-7-(2-methyltetrazol-5-yl)-9H-pyrimido[4,5-b]indol-4-yl]cyclohexane-1,4-diamine (hereinafter, also referred to as "UM171"). In an embodiment of the present invention, a culture medium used in the culture method of the present invention does not further comprise UM171. Consequently, human hematopoietic stem cells are easily differentiated into megakaryocytic lineage cells (e.g., megakaryocytes precursor cells or megakaryocytes).

In the present invention, human hematopoietic stem cells can be cultured under a condition suited for proliferation of human hematopoietic stem cells. In the present invention, a method may further comprise isolating human hematopoietic stem cells from a culture. Human hematopoietic stem cells can be isolated by a method known to those skilled in the art, for example, by methods such as flow cytometry using a hematopoietic stem cell marker. Human hematopoietic stem cells may be collected as human hematopoietic stem cells, or may be further differentiated into other cells and used later. When human hematopoietic stem cells are differentiated into other cells, cells to be differentiated can be cultured under a condition suited for differentiation into the above-mentioned other cells.

According to the present invention, a human hematopoietic stem cells obtained by the culture method of the present invention is provided. The human hematopoietic stem cell obtained by the culture method of the present invention can be purified using CD34, preferably together with CD38, as a marker. The human hematopoietic stem cell obtained by the culture method of the present invention achieves a higher survival rate after transplantation into a recipient than human hematopoietic stem cells obtained by conventional methods. Therefore, according to the present invention, a human hematopoietic stem cell is provided that is obtained by the culture method of the present invention and has an improved survival rate after transplantation into a recipient as compared with cells before culture.

According to the present invention, a megakaryocytic lineage cell (e.g., megakaryocytes precursor cell or megakaryocyte) obtained by the culture method of the present invention is provided. Megakaryocytic lineage cells can be differentiated into multinucleated megakaryocytes by a usual method. Platelets can be obtained from multinucleated megakaryocytes. In the present invention, a method may further comprise isolating megakaryocytic lineage cells from an obtained culture. Megakaryocytic lineage cells can be isolated by a method known to those skilled in the art, for example, by flow cytometry using a megakaryocytic lineage cell marker (e.g., CD41a and CD42b).

In the culture method of the present invention, culture can be performed in the presence of fibronectin. In the culture method of the present invention, cells are cultured under a condition where hematopoietic stem cells can be brought into contact with fibronectin. In the culture method of the present invention, preferably, for example, the inside (e.g., a bottom surface) of a culture container is coated with fibronectin for culture.

An albumin-free medium used in the culture method of the present invention comprises serum albumin only in an amount of lower than 0.1% (w/v), lower than 0.05% (w/v), lower than 0.01% (w/v), lower than 0.005% (w/v), lower than 0.001% (w/v), lower than 0.0005% (w/v), or lower than 0.0001% (w/v) or comprises no serum albumin at all.

A medium used in the culture method of the present invention may comprise a recombinant TPO. For example, a recombinant TPO can be a recombinant TPO of a mammal or a recombinant human TPO. In an embodiment of the present invention, the TPO concentration is 20 to 200 ng/mL, more preferably 30 to 150 ng/mL, yet more preferably 40 to 150 ng/mL, and can be, for example, 100 ng/mL.

A medium used in the culture method of the present invention may further comprise a recombinant SCF. For example, a recombinant SCF can be a recombinant SCF of a mammal or a recombinant human SCF. In an embodiment of the present invention, the SCF concentration is 1 to 200 ng/mL, more preferably 1 to 150 ng/mL, yet more preferably 1 to 100 ng/mL, for example, 1 to 50 ng/mL, yet more preferably 1 to 30 ng/mL, yet more preferably 1 to 20 ng/mL, and can be, for example, 5 to 15 ng/mL.

A medium used in the culture method of the present invention may comprise a recombinant TPO and a recombinant SCF. In this embodiment, the TPO concentration is 20 to 200 ng/mL, more preferably 30 to 150 ng/mL, yet more preferably 40 to 150 ng/mL, and can be, for example, 100 ng/mL; and the SCF concentration is 1 to 200 ng/mL, more preferably 1 to 150 ng/mL, yet more preferably 1 to 100 ng/mL, for example, 1 to 50 ng/mL, yet more preferably 1 to 30 ng/mL, yet more preferably 1 to 20 ng/mL, and can be, for example, 5 to 15 ng/mL. In a preferred embodiment, a medium used in the culture method of the present invention may comprise 40 to 150 ng/mL recombinant TPO and 1 to 50 ng/mL recombinant SCF. In a preferred embodiment, in a medium used in the culture method of the present invention, the TPO concentration is higher than the SCF concentration, can be, for example, any concentration within the above-mentioned range of concentrations, and may be higher 2-fold or more, 3-fold or more, 4-fold or more, 5-fold or more, 6-fold or more, 7-fold or more, 8-fold or more, 9-fold or more, or 10-fold or more.

The method of culturing human hematopoietic stem cells of the present invention can further comprise proliferating hematopoietic stem cells under a condition adequate for maintenance and/or proliferation of hematopoietic stem cells. In this embodiment, for example, the method can comprise proliferating hematopoietic stem cells 10-fold or more, 50-fold or more, 100-fold or more, 200-fold or more, 300-fold or more, 400-fold or more, or 500-fold or more relative to the start of culture.

The condition adequate for maintenance and/or proliferation of human hematopoietic stem cells can be, for example, a condition where cells are cultured in the above-mentioned media. The condition adequate for maintenance and/or proliferation of human hematopoietic stem cells can be, preferably, for example, a condition where fibronectin exists, and a condition where human hematopoietic stem cells can be brought into contact with fibronectin.

The culture method of the present invention may further comprise (C) recovering proliferated human hematopoietic stem cells from the medium.

The recovered human hematopoietic stem cells may be further concentrated or isolated. Human hematopoietic stem cells can be concentrated or isolated using a cell surface marker. Examples of a cell surface marker that can be used for concentration or isolation of human hematopoietic stem cells include CD34 and CD38. Hematopoietic stem cells can be concentrated or isolated using a cell sorter.

According to the present invention, a method for manufacturing human hematopoietic stem cells ex vivo, comprising the culture method of the present invention, is provided. In the manufacturing method of the present invention, functional human hematopoietic stem cells can be obtained. The term "functional" used herein means that the hematopoietic system can be recovered in a human body receiving transplantation (recipient) by transplantation of human hematopoietic stem cells.

EXAMPLES

Example 1: Assay for Proliferation of Hematopoietic Stem Cells Using a Culture Medium not Comprising Albumin In this example, an assay was performed in which mouse hematopoietic stem cells (KSL cells) and human hematopoietic stem cells (CD34$^+$CD38$^-$ cells) were allowed to proliferate in a culture medium not comprising albumin. The culture medium was a serum-free medium comprising polyvinyl alcohol (PVA) and not comprising albumin, as described in Wilkinson et al., Nature, 571:117-121, 2019.

Specifically, the culture medium used for culture of mouse hematopoietic stem cells was an F12 medium comprising 1% insulin-transferrin-selenium-ethanolamine (ITSX), 10 mM HEPES, 1% penicillin-streptomycin-glutamine, 100 ng/mL mouse thrombopoietin (mTPO), and 10 ng/mL mouse stem cell factor (mSCF). The medium comprised PVA at the final concentration of 0.1%. The culture medium used for culture of human hematopoietic stem cells was an IMDM medium comprising 1% insulin-transferrin-selenium-ethanolamine (ITSX), 25 mM HEPES, 1% penicillin-streptomycin-glutamine, 100 ng/mL human thrombopoietin (hTPO), and 10 ng/mL human stem cell factor (hSCF). The medium comprised PVA at the final concentration of 0.1%.

Unless otherwise specified, all media used in the following examples were an IMDM medium comprising 1% insulin-transferrin-selenium-ethanolamine (ITSX), 25 mM HEPES, 1% penicillin-streptomycin-glutamine, and PVA (hereinafter, also referred to as "common medium"). Therefore, hereinafter, description of the medium will be focused on components added to the common medium. For example, given that the above-mentioned medium comprises TPO and SCF in addition to the common medium, it is to be referred to as a TPO+SCF medium for the purpose of convenience. When the concentration of each factor is expressed, a medium may be referred to as SCF10+TPO100 or may also be referred to as S10+T100 as an abbreviated form.

As mouse hematopoietic stem cells, KSL cells derived from mouse bone marrow were used. Specifically, mouse bone marrow cells were isolated from the tibia, femur, and pelvis and stained with an APC-c-KIT antibody. c-KIT$^+$ cells were concentrated using anti-APC magnetic beads and an LS column (Miltenyi Biotec). Then, the concentrated c-KIT cells were stained with a lineage antibody cocktail (biotinylated CD4, CD8, CD45R, TER119, LY-6G/LY-6C, and CD127) before being stained with anti-CD34, anti-c-KIT, anti-SCA1, and streptavidin-APC-eFluor 780 for 90 minutes. Then, cells were screened directly and purified in a medium-containing well using FACS Aria II (BD) for cell populations and propidium iodide for dead cells.

As human hematopoietic stem cells, human bone marrow CD34+CD38$^-$ cells were used. Specifically, commercially available human bone marrow CD34-positive cells (Lonza 2C-101) were purchased.

The results are as shown in FIG. 1. In Wilkinson et al., 2019, long-term proliferation of mouse hematopoietic stem cells could not be maintained even in the presence of SCF and TPO in a serum-free medium not comprising albumin. However, Wilkinson et al., 2019 showed that mouse hematopoietic stem cells could proliferate in a serum-free medium not comprising albumin for a long period of time by adding PVA to the medium. As shown in FIG. 1, mouse hematopoietic stem cells favorably proliferated in a serum-free medium comprising PVA and not comprising albumin, but favorable proliferation of human hematopoietic stem cells was not observed in this medium.

Example 2: Difference in Signal Transduction Between Mouse Hematopoietic Stem Cells and Human Hematopoietic Stem Cells The signaling pathways were analyzed in mouse hematopoietic stem cells and human hematopoietic stem cells in the presence of SCF and TPO.

Mouse and human hematopoietic stem cells were cultured in the presence of 10 ng/mL tissue factor (i.e., SCF) and 100 ng/mL thrombopoietin (TPO) in the absence of albumin and in the presence of PVA, and the extents of phosphorylation of signal factors downstream of SCF and TPO in the hematopoietic stem cells were analyzed by a phosphorylation immunostaining method. First, the phosphorylation status of each factor downstream of the SCF and TPO signals was detected using an antibody specific to the phosphorylated form of each factor. Specifically, cells stimulated with a cytokine were allowed to react with a phosphorylation antibody in representative signal transduction molecules such as Akt, PI3K, and Stat5, and then the fluorescence intensity of the antibody allowed to react with cells was quantitatively analyzed under a fluorescence microscope.

Figure 2:
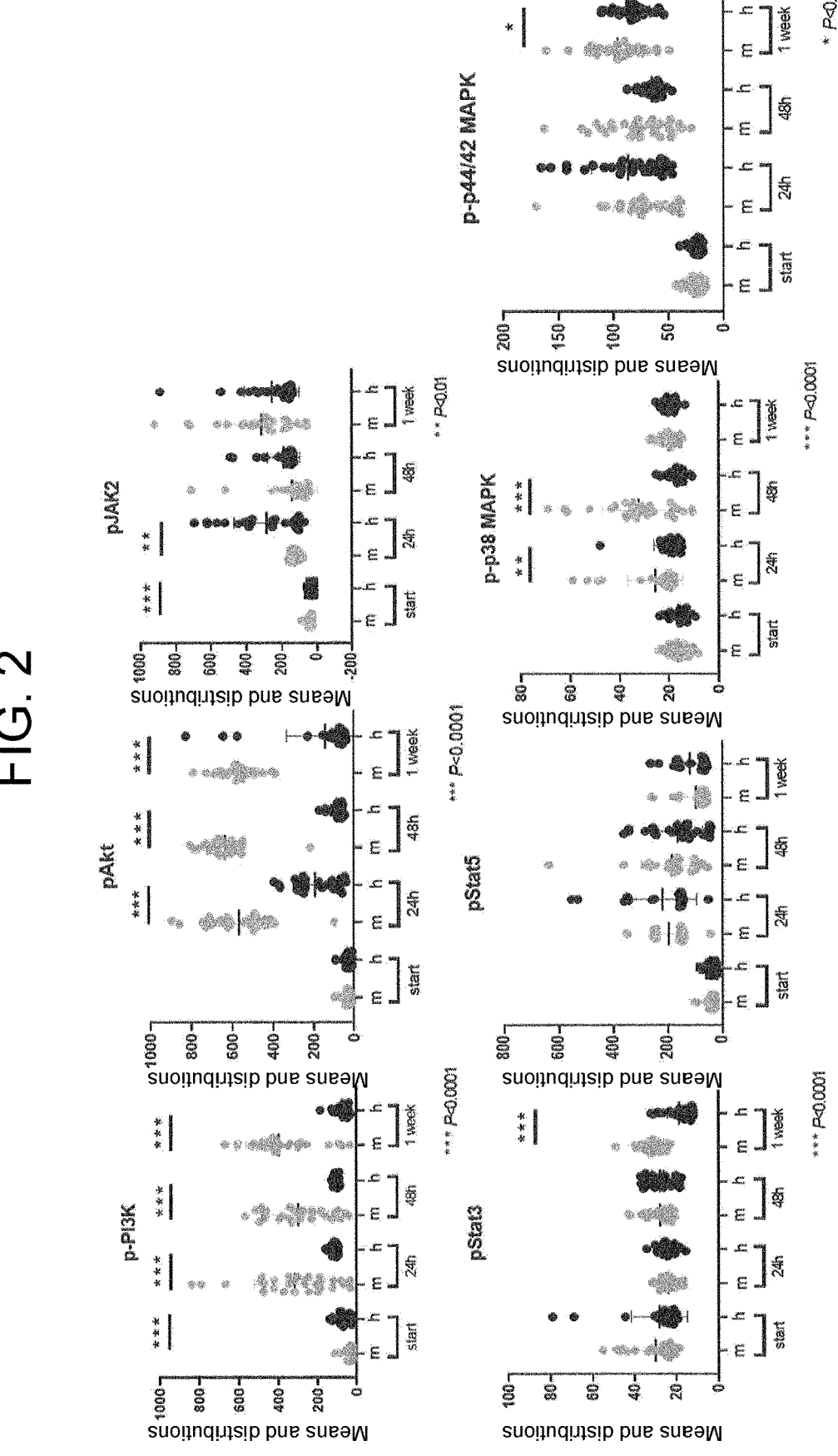
FIG. 2 shows the extent of phosphorylation of downstream signal factors for SCF and TPO in hematopoietic stem cells obtained by culturing mouse and human hematopoietic stem cells in the presence of 10 ng/mL tissue factor (i.e., SCF) and 100 ng/mL thrombopoietin (TPO) in the absence of albumin and in the presence of PVA. The symbol "m" denotes mouse hematopoietic stem cells, and "h" denotes human hematopoietic stem cells.

Then, as shown in FIG. 2, some of the seven examined factors were found to be different in phosphorylation status between mouse hematopoietic stem cells and human hematopoietic stem cells. Among these factors, many phosphorylated forms of PI3K and Akt were observed in mouse hematopoietic stem cells from 24 hours after adding SCF and TPO, whereas substantially no phosphorylated forms were observed in human hematopoietic stem cells, or phosphorylated forms were observed in an amount less than the amount of phosphorylated forms in mouse hematopoietic stem cells.

Figure 3:
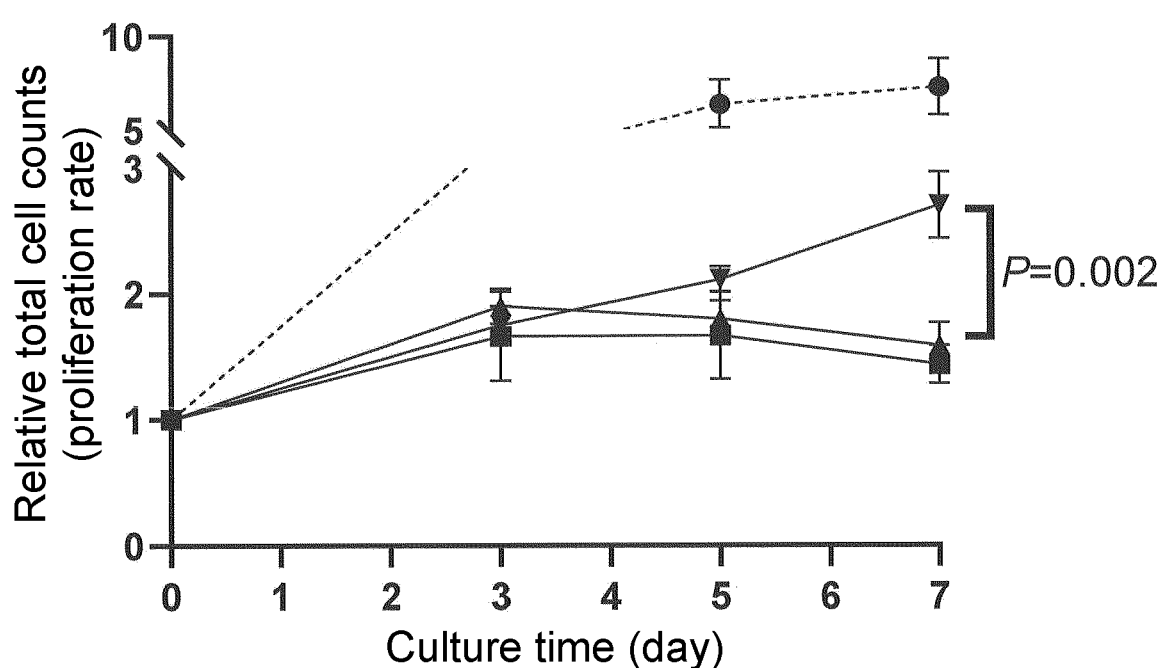
FIG. 3 shows the results of culturing human hematopoietic stem cells in the presence of 10 ng/mL human tissue factor (i.e., SCF), 100 ng/mL human thrombopoietin (TPO), and AKT activator II (AKTa) or a PI3K activator (PI3Ka) in the absence of albumin and in the presence of PVA.

Accordingly, human hematopoietic stem cells were cultured in a culture medium comprising 0.3 μM AKTa (name of distributer, Sigma-Aldrich; product number 123871) or 20 μM PI3Ka. Cells were counted after 3 days, 5 days, and 7 days of culture, and the ratios of the number of cells at each time point to the number of cells on the first day of culture, which was standardized as 1, were obtained. In the following example, 740Y-P (name of distributer, Tocris; product number 1983) was used as PI3Ka. Then, as shown in FIG. 3, human hematopoietic stem cells clearly proliferated in the presence of PI3Ka. In contrast, AKTa did not show a proliferative effect on human hematopoietic stem cells in the environment of this experiment.

Figure 4:
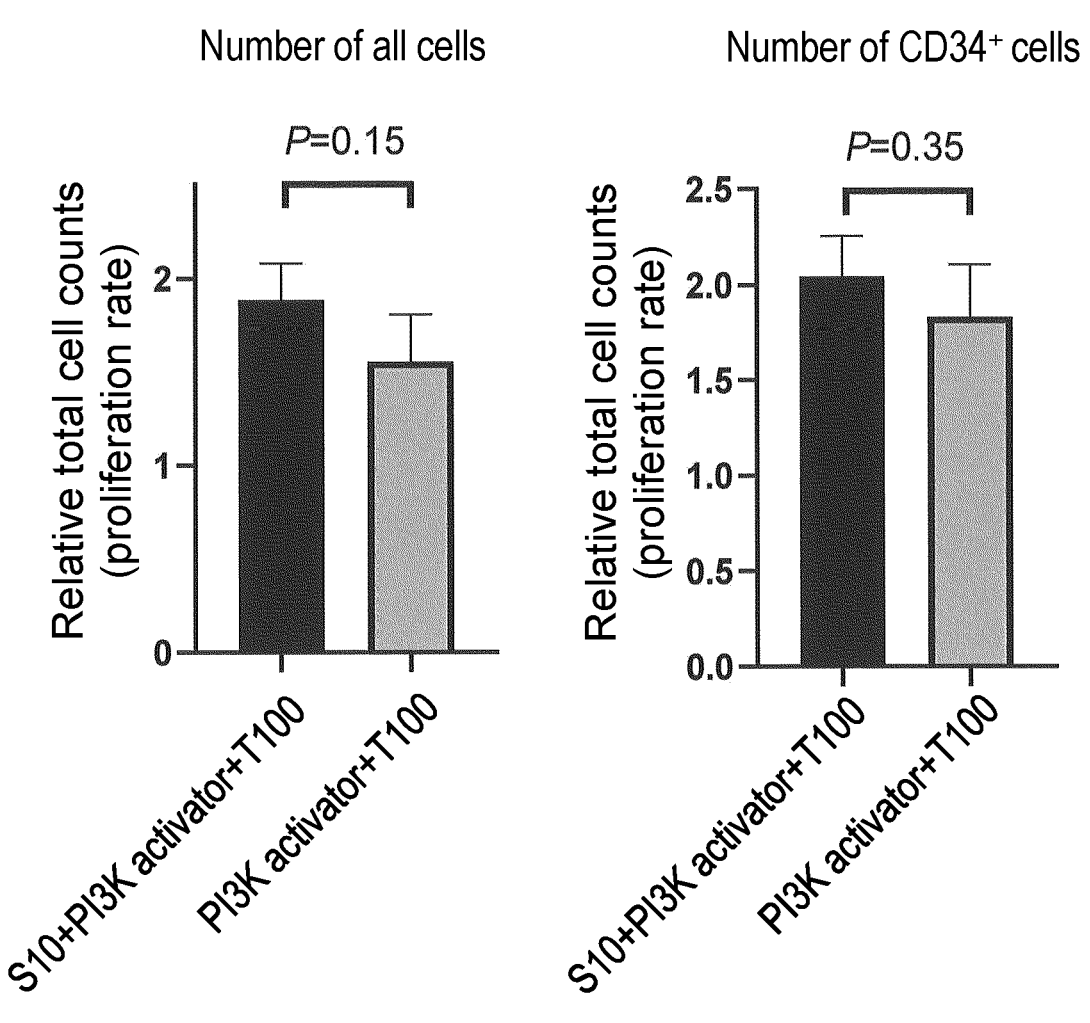
FIG. 4 shows the proliferation rates of total cells and CD34$^+$ cells at day 7 of culturing human hematopoietic stem cells in the presence of 100 ng/mL human thrombopoietin (TPO), in the absence of albumin and in the presence of PVA.

Subsequently, whether or not PI3Ka completely replaced SCF in culture of human hematopoietic stem cells was examined. Human hematopoietic stem cells were cultured for 7 days in the above-mentioned culture medium for human hematopoietic stem cells which comprised 20 μM PI3Ka (S10+PI3Ka20+T100) or which comprised 20 μM PI3Ka and did not comprise SCF (PI3Ka20+T100), and then the number of total cells and the number of CD34+ cells, which were isolated by cell sorting using an anti-CD34 antibody, were compared. The results were as shown in FIG. 4. As shown in FIG. 4, when PI3Ka was added, no significant difference was found in the number of total cells or the number of CD34+ cells whether SCF was present or not.

Figure 5:
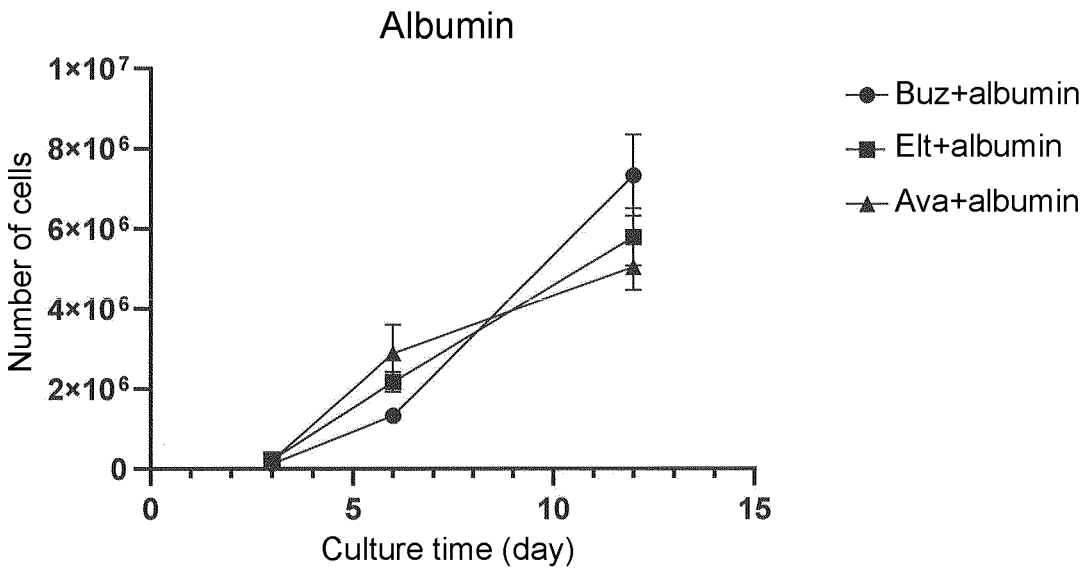
FIG. 5 shows the change with time in the number of cells when human hematopoietic stem cells were cultured in the presence of either albumin or PVA with various TPO receptor agonists as TPO replacements. The symbol "Buz" denotes butyzamide, "Elt" denotes eltrombopag, and "Ava" denotes avatrombopag.
Figure 5:
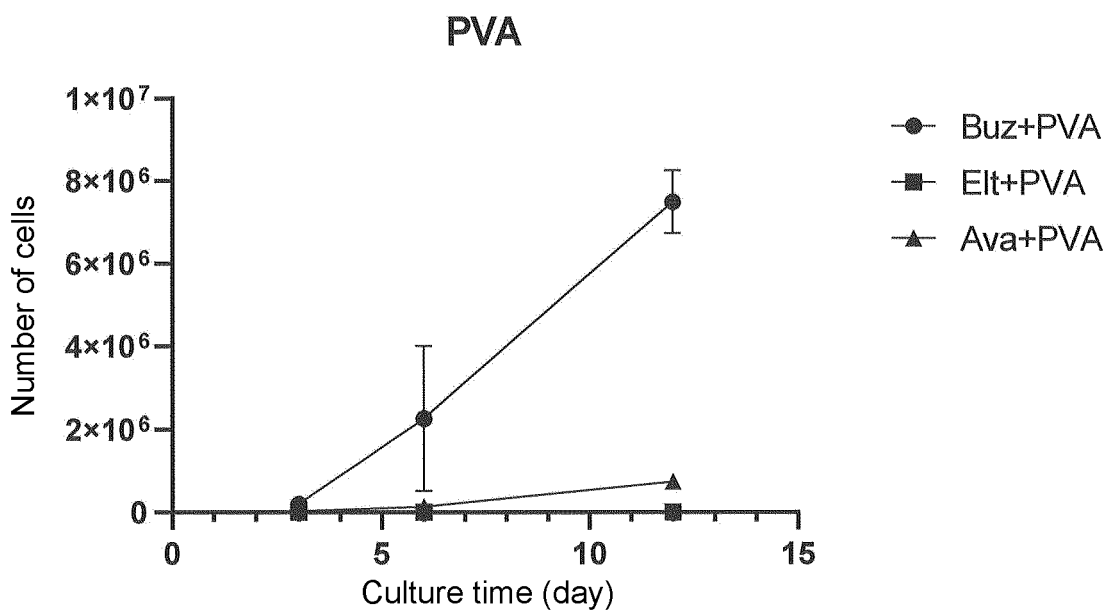

Subsequently, whether or not TPO can be replaced with a TPO receptor agonist in culture of human hematopoietic stem cells was examined. Butyzamide, eltrombopag, and avatrombopag are known as TPO receptor agonists. Human hematopoietic stem cells were cultured in the presence of 0.1% recombinant human serum albumin (Albumin Biosciences) or in the presence of PVA in the above-mentioned culture medium having a composition from which TPO was removed and to which 0.1 μM butyzamide, 3 μg/mL eltrombopag, or 3 μM avatrombopag was added. In this experiment, Mpl32D cells were used as human hematopoietic stem cells. The results were as shown in FIG. 5. As shown in FIG. 5, butyzamide, eltrombopag, and avatrombopag could support proliferation of human hematopoietic stem cells in the presence of albumin and in the absence of TPO. In contrast, in the presence of PVA (in the absence of albumin) and in the absence of TPO, butyzamide showed a marked proliferative effect on human hematopoietic stem cells, but avatrombopag showed a low effect thereon, and eltrombopag showed substantially no such effect.

Figure 6:
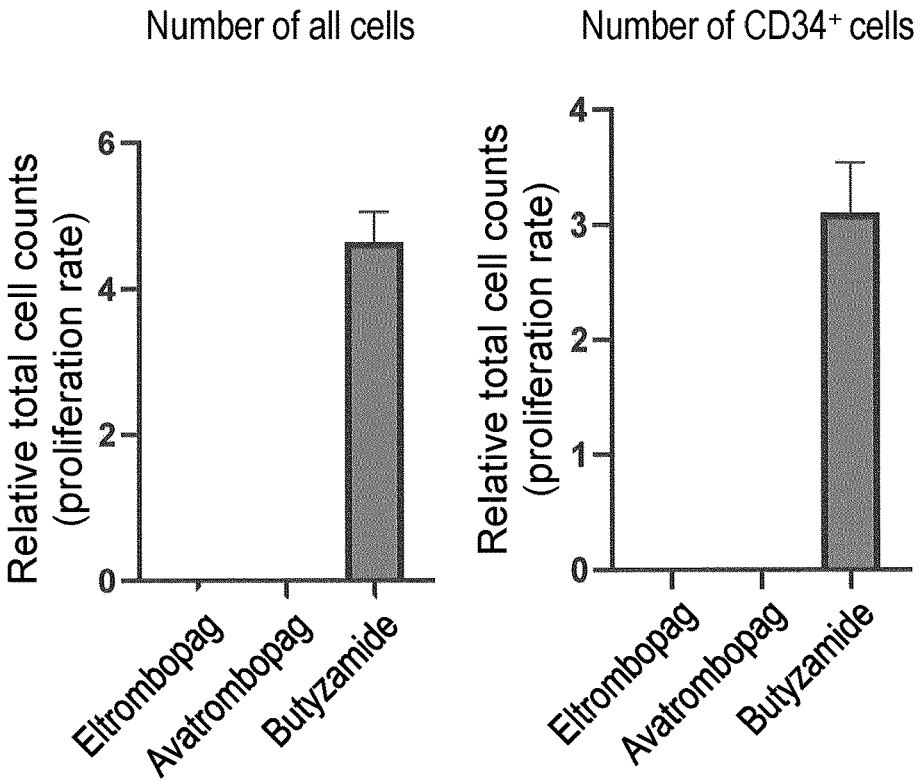
FIG. 6 shows the proliferation rates of total cells and CD34$^+$ cells at day 7 when human hematopoietic stem cells were cultured in the presence of either albumin or PVA with various TPO receptor agonists as TPO replacements.

Further, purchased human bone marrow CD34+ cells (distributor name, Lonza; product number 2C-101) or CD34+ cells isolated from given fresh umbilical cord blood using microbeads were used in the culture experiment. The cells were dispensed to a 24-well plate at 0.2 to 1.0×10^5 cells per well, TPO was removed from a culture medium for human hematopoietic stem cells and replaced with any of the above-mentioned TPO receptor agonists (hereinafter, may be referred to as "TPOago") to perform the experiment. The ratio of the number of cells at day 7 of culture relative to the first day of culture was obtained. The results were as shown in FIG. 6. As shown in FIG. 6, human hematopoietic stem cells significantly proliferated only in the presence of butyzamide, in the absence of albumin and in the presence of PVA. Death of hematopoietic stem cells occurred in the presence of avatrombopag or in the presence of eltrombopag in the absence of albumin and in the presence of PVA.

However, these TPO receptor agonists are highly safe compounds in a biological environment and used for surgical treatment of patients with liver cirrhosis and treatment of patients with aplastic anemia. The results of this example indicate that some TPO receptor agonists can exhibit cytotoxicity against human hematopoietic stem cells in the absence of albumin and in the presence of PVA. Additionally, this suggests that some TPO receptor agonists are cytotoxic against human hematopoietic stem cells, and that those not cytotoxic against human hematopoietic stem cells can be used to culture human hematopoietic stem cells.

Figure 7:
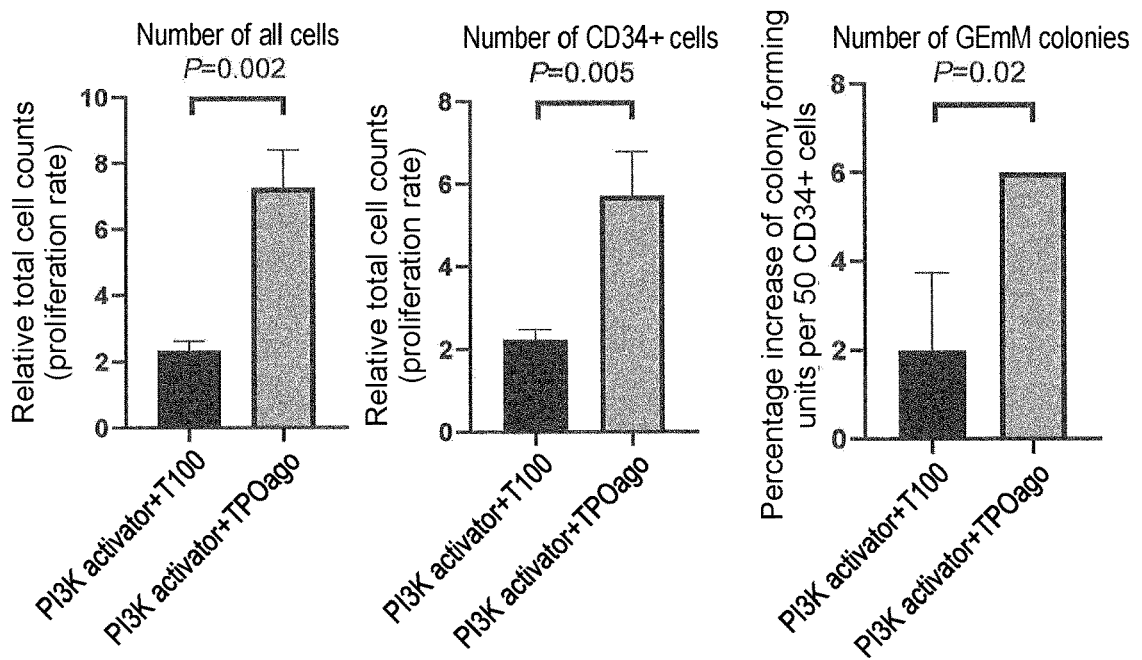
FIG. 7 shows the number of total cells, the number of CD34$^+$ cells, and the number of GEmM colonies at day 7 when human hematopoietic stem cells were cultured in the absence of albumin and in the presence of PVA in a medium comprising a PI3K activator and TPO or butyzamide (Buty). The types of colonies were determined under a microscope by performing Giemsa staining after colonies were collected under a microscope, and cytospin specimens were prepared. G denotes "granulocyte," E denotes "erythroblast," m denotes "macrophage," and M denotes "megakaryocyte."

Subsequently, whether or not SCF and TPO can be replaced with PI3Ka and a TPO receptor agonist in the absence of albumin and in the presence of PVA was examined. In the following example, butyzamide was used as a TPO receptor agonist. Purchased human bone marrow CD34+ cells (distributor name, Lonza; product number 2C-101) or CD34+ cells isolated from given fresh umbilical cord blood using microbeads as described above were used in the culture experiment. The cells were dispensed to a 24-well plate at 0.2×10^5 to 1.0×10^5 cells per well and cultured in a medium having a composition in which SCF was replaced with 20 μM PI3Ka (PI3Ka20 μM+TPO100) and a medium having a composition in which SCF was replaced with 20 μM PI3Ka and TPO was replaced with 0.1 μM butyzamide (PI3Ka20 μM+TPOago0.1 μM). Seven days later, the number of total cells was obtained, and the number of CD34+ cells was obtained by flow cytometry. Then, the proliferation rate compared with the start of culture was obtained. The results were as shown in FIG. 7. As shown in FIG. 7, it was found that butyzamide could completely replace TPO. Further, CD34+ cells were sorted with a cell sorter before and after culture, 100 cells each were seeded in a MethoCult™ H4415 medium, and a colony assay was performed. Two weeks later, colonies were picked up, cytospin specimens were prepared, Giemsa staining was performed, and then the types of colonies were determined under a microscope. The number of GEmM colonies per 50 CD34+ cells was counted, and the percentage increase in the number of colonies compared with before culture was obtained. Then, it was found that butyzamide could completely replace TPO in view of the GEmM colony forming ability.

Figure 8:
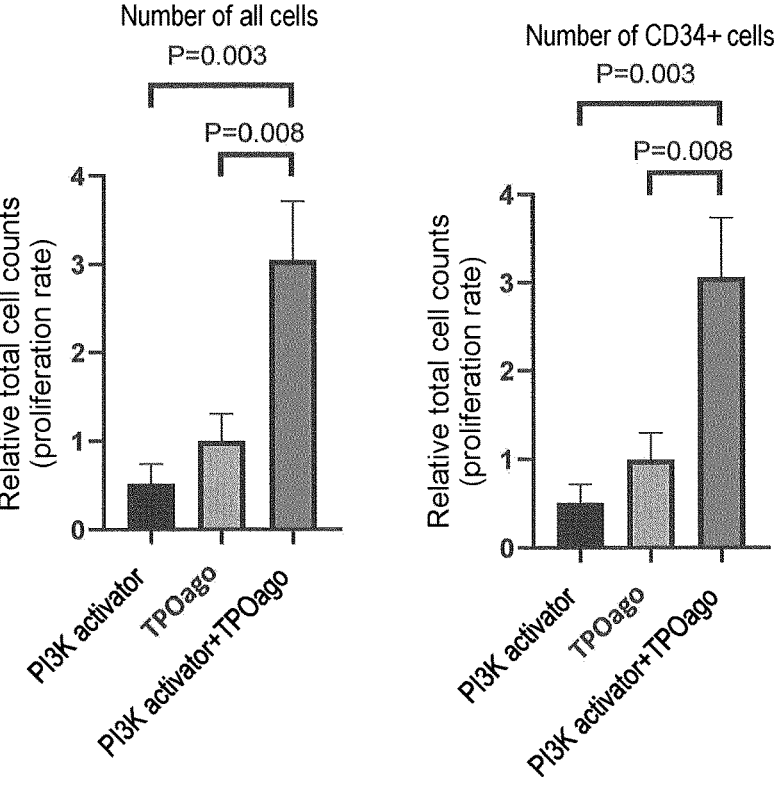
FIG. 8 shows the proliferation rates of total cells and CD34$^+$ cells at day 7 when human hematopoietic stem cells were cultured in the absence of albumin and in the presence of PVA in a culture medium comprising neither SCF nor TPO but comprising a PI3K activator or a TPO receptor agonist or a combination thereof.

Further, subsequently, a culture experiment of human hematopoietic stem cells was performed in a culture medium comprising neither SCF nor TPO to which 20 μM PI3Ka or 0.1 μM TPOago or both were added. At day 7 of culture, the number of total cells and the number of CD34+ cells included therein were counted by flow cytometry, and the proliferation rates relative to the start of culture were obtained. Then, as shown in FIG. 8, increases of cells were not observed in the presence of PI3Ka alone or butyzamide alone, but the number of cells markedly increased in the presence of both PI3Ka and TPOago.

Figure 9:
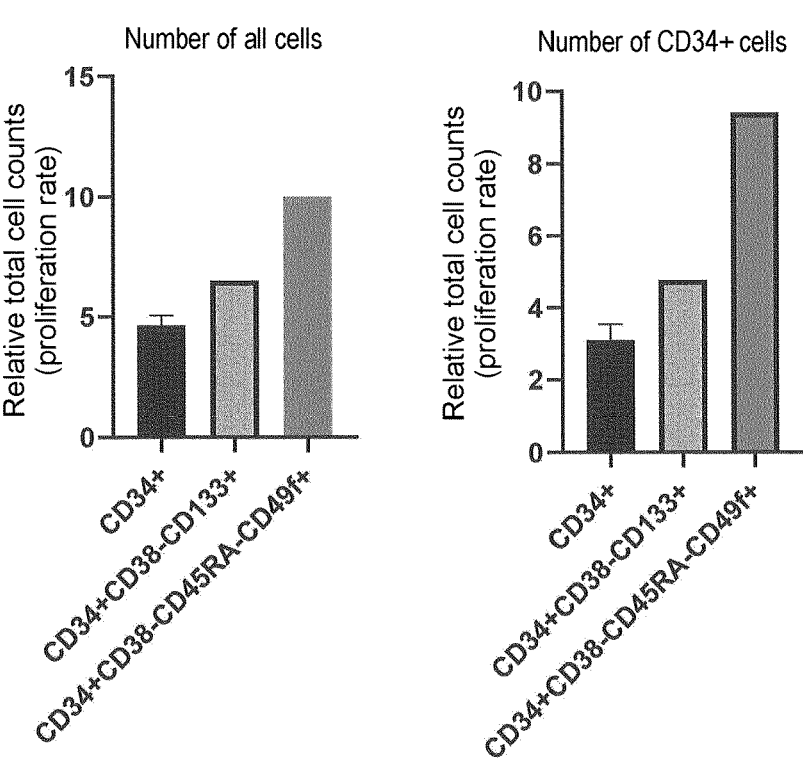
FIG. 9 shows the proliferation rate of each cell population in the culture obtained at day 7 when human hematopoietic stem cells were cultured in the absence of albumin and in the presence of PVA in a culture medium comprising neither SCF nor TPO but comprising a PI3K activator and a TPO receptor agonist.

Further, subsequently, which cell population easily proliferated in a medium in which SCF and TPO were replaced with PI3Ka and TPOago was examined. CD34+ cells isolated from given fresh umbilical cord blood using microbeads as described above were used in the culture experiment. Cells were fractioned with a cell sorter using anti-CD34-PE-Cy7 antibody (distributor name, BD Biosciences; product number 348791), anti-CD38-V450 antibody (distributor name, BD Biosciences; product number 646851), anti-CD133-PE antibody (distributor name, Miltenyi Biotec; product number 130-080-801), anti-CD45RA-APC antibody (distributor name, BioLegend; product number 304112), and anti-CD49f-PE antibody (distributor name, BioLegend; product number 313611). For each of the CD34$^+$ fraction, CD34+CD38$^-$CD133$^+$ fraction, and CD34$^+$ CD38$^-$CD45RA$^-$CD49f$^+$ fraction reported as purification markers of human umbilical cord blood-derived hematopoietic stem cells, the number of total cells and the number of CD34+ cells included therein were counted by flow cytometry at day 7 after the start of culture, and the proliferation rates relative to the start of culture were obtained. The results were as shown in FIG. 9. As shown in FIG. 9, significant cell proliferation was observed in any cell fraction, and cell proliferation was remarkable in the CD34$^+$CD38$^-$CD133$^+$ fraction and the CD34$^+$CD38$^-$CD45RA$^-$ CD49f$^+$ fraction, particularly in the CD34+CD38$^-$CD45RA$^-$ CD49f$^+$ fraction.

Example 3: Long-Term Culture Experiment of Human Hematopoietic Stem Cells

Figures 10, 11:
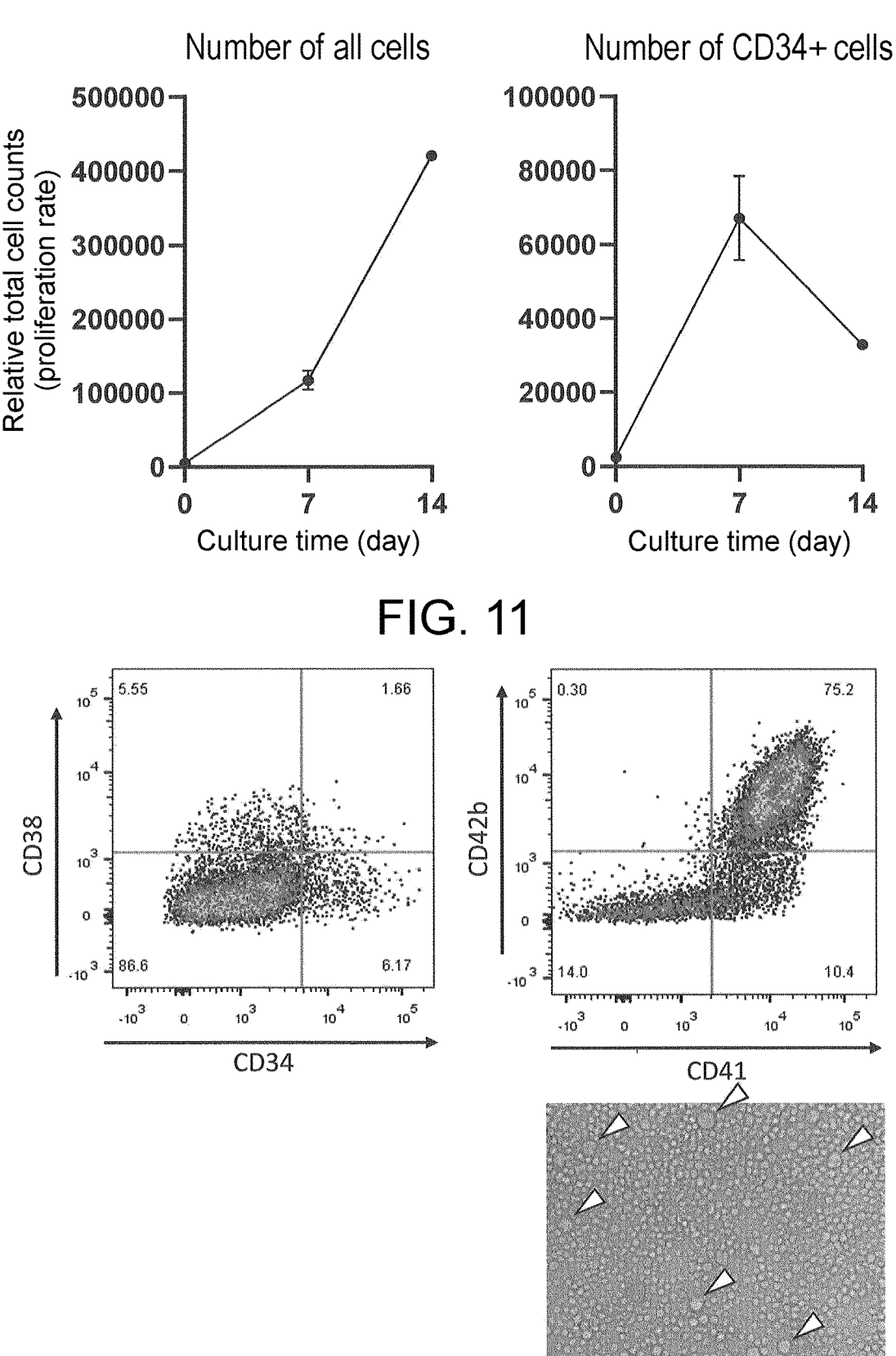
FIG. 10 shows the changes with time in the number of total cells and the change with time in the number of CD34$^+$ cells at day 7 and day 14 when human hematopoietic stem cells were cultured in the absence of albumin and in the presence of PVA in a culture medium comprising neither SCF nor TPO but comprising a PI3K activator and a TPO receptor agonist.
FIG. 11 shows the results of gating of cells obtained at day 14 when human hematopoietic stem cells were cultured in the absence of albumin and in the presence of PVA in a culture medium comprising neither SCF nor TPO but comprising a PI3K activator and a TPO receptor agonist. The left panel shows the result of flow cytometry using CD34 and CD38 as markers, and the right panel shows the result of flow cytometry using CD41a and CD42b as markers. The photograph in FIG. 11 is an optical micrograph of the obtained culture.

Human hematopoietic stem cells were cultured in the above-mentioned culture medium for human hematopoietic stem cells which comprised 20 μM PI3Ka and 0.1 μM TPOago instead of SCF and TPO. The number of total cells and the number of CD34$^+$ cells were obtained in the same way as described above at day 7 and day 14 after the start of culture. The results were as shown in FIG. 10. As shown in FIG. 10, the number of total cells increased with a greater number of culture days, while the number of CD34$^+$ cells was lower at day 14 than at day 7.

When the cultured cells were observed using an optical microscope, huge cells were observed at day 14. To confirm the possibility that these huge cells are megakaryocytes or precursor cells of megakaryocytes, cells were fractioned with a flow cytometer using anti-CD41a-FITC antibody (distributor name, BD Pharmingen Inc.; product number 555466) and anti-CD42b antibody (distributor name, BD Pharmingen Inc.; product number 555473). As shown in FIG. 11, the results demonstrated that the majority of cells were CD41a$^+$CD42b$^+$ cells at day 14 after the start of culture. However, as shown in FIG. 11, CD34$^+$CD38$^-$ cells also proliferated under this condition.

Figure 12:
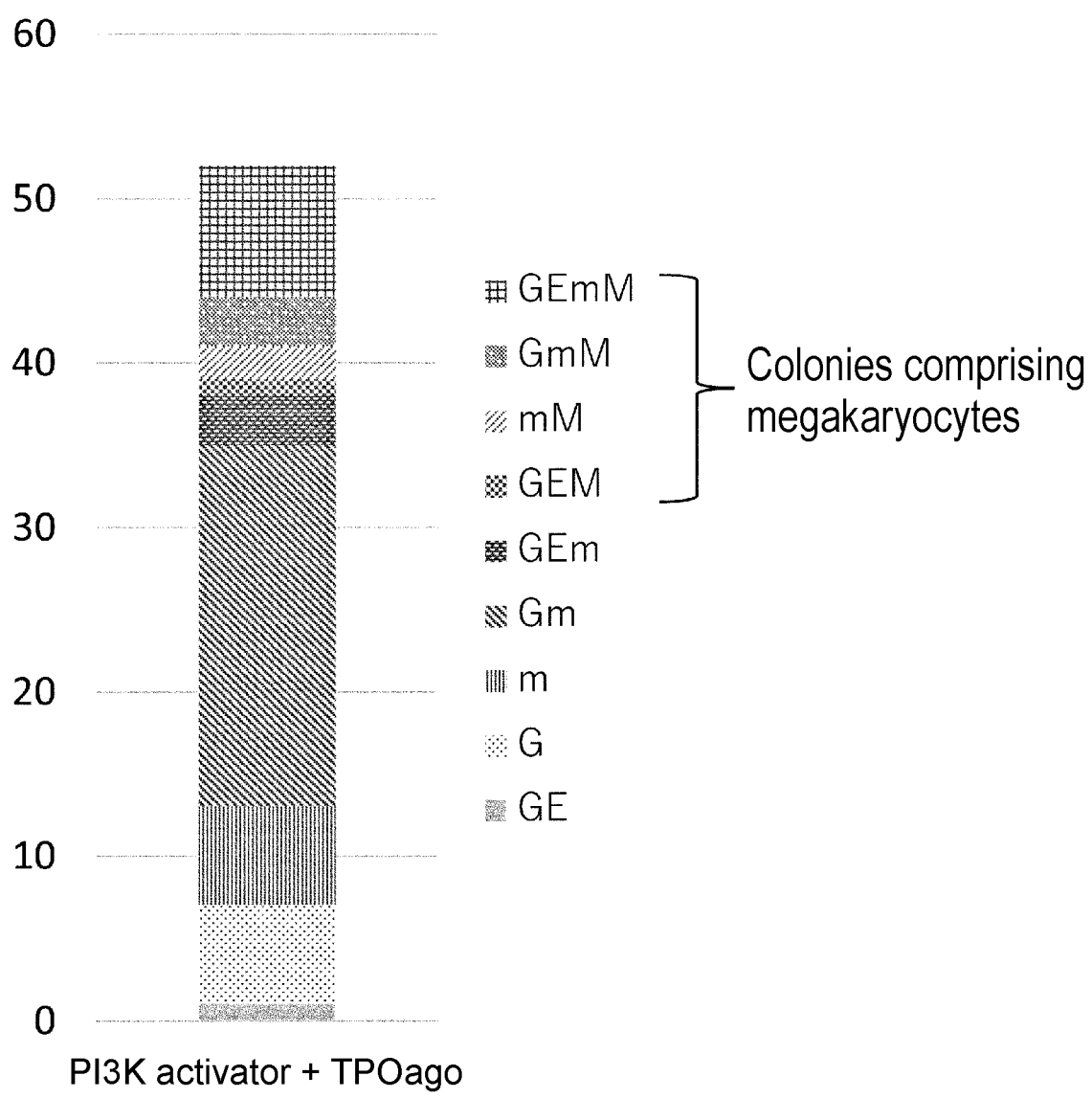
FIG. 12 shows the result of a colony assay of cells obtained at day 14 when human hematopoietic stem cells were cultured in the absence of albumin and in the presence of PVA in a culture medium comprising neither SCF nor TPO but comprising a PI3K activator and a TPO receptor agonist. The types of colonies were determined under a microscope by performing Giemsa staining after colonies were collected under a microscope, and cytospin specimens were prepared. G denotes the colonies comprising "granulocyte," E denotes the colonies comprising "erythroblast," m denotes the colonies comprising "macrophage," and M denotes the colonies comprising "megakaryocyte."

Further, 100 CD34+ cells obtained in the culture at day 14 after the start of culture were seeded each on a MethoCult™ H4415 medium, and a colony assay was performed. Colonies were collected 2 weeks later to prepare cytospin specimens. Then, after Giemsa staining was performed for the specimens, the types of colonies were determined under a microscope. The results were as shown in FIG. 12. The types of colonies are expressed as follows: G denotes a colony comprising "granulocytes," E denotes a colony comprising "erythroblasts," m denotes a colony comprising "macrophages," and M denotes a colony comprising "megakaryocytes." As shown in FIG. 12, many of the cell colonies were colonies comprising megakaryocytes.

Example 4: Examination of Conditions More Suited for Long-Term Culture of Human Hematopoietic Stem Cells Long-term culture of human hematopoietic stem cells was attempted in the presence of compounds that can proliferate human hematopoietic stem cells.

Figure 13:
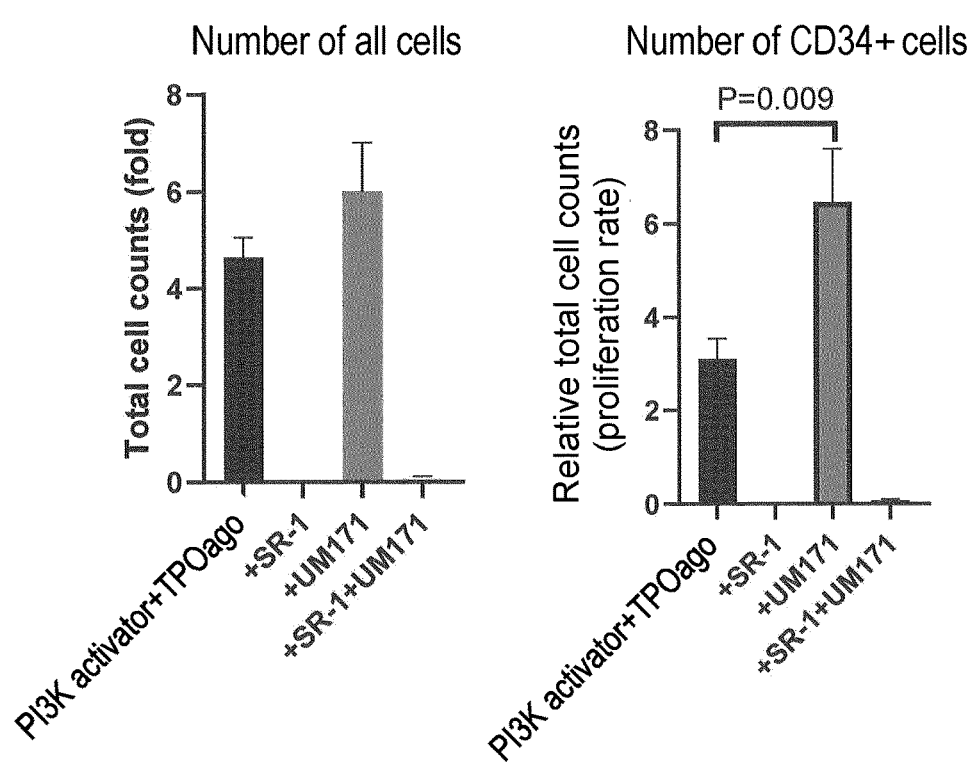
FIG. 13 shows the proliferation rates of total cells and CD34$^+$ cells at day 14 when human hematopoietic stem cells were cultured in the absence of albumin and in the presence of PVA in a culture medium comprising neither SCF nor TPO but comprising a PI3K activator; a TPO receptor agonist; and either SR-1 or UM171 or both thereof.

Media were prepared by adding 20 μM PI3Ka and 0.1 μM TPOago instead of SCF and TPO to the above-mentioned culture medium for human hematopoietic stem cells (20 μMPI3Ka+0.1 μMTPOago) and further adding either SR-1 (500 nM) or UM171 (35 nM) or both (+SR-1, +UM171, or +SR-1+UM171). Purchased human bone marrow CD34$^+$ cells (distributor name, Lonza; product number 2C-101) or CD34$^+$ cells isolated from given fresh umbilical cord blood using microbeads as described above were used for culture experiment. The cells were dispensed to a 24-well plate at $0.2 \times 10^5$ to $1.0 \times 10^5$ cells per well, and CD34$^+$ cells were cultured in the prepared media. The number of total cells and the number of CD34$^+$ cells were counted at day 14 after the start of culture in the same way as described above, and the proliferation rates relative to before the start of culture were obtained. The results were as shown in FIG. 13. As shown in FIG. 13, in the culture medium further comprising UM171, the number of total cells and the number of CD34$^+$ cells increased, and the percentage increase of CD34$^+$ cells in the medium comprising UM171 significantly increased as compared with that in the media not comprising UM171. In contrast, SR-1 killed cells under the conditions of this experiment.

Figure 14:
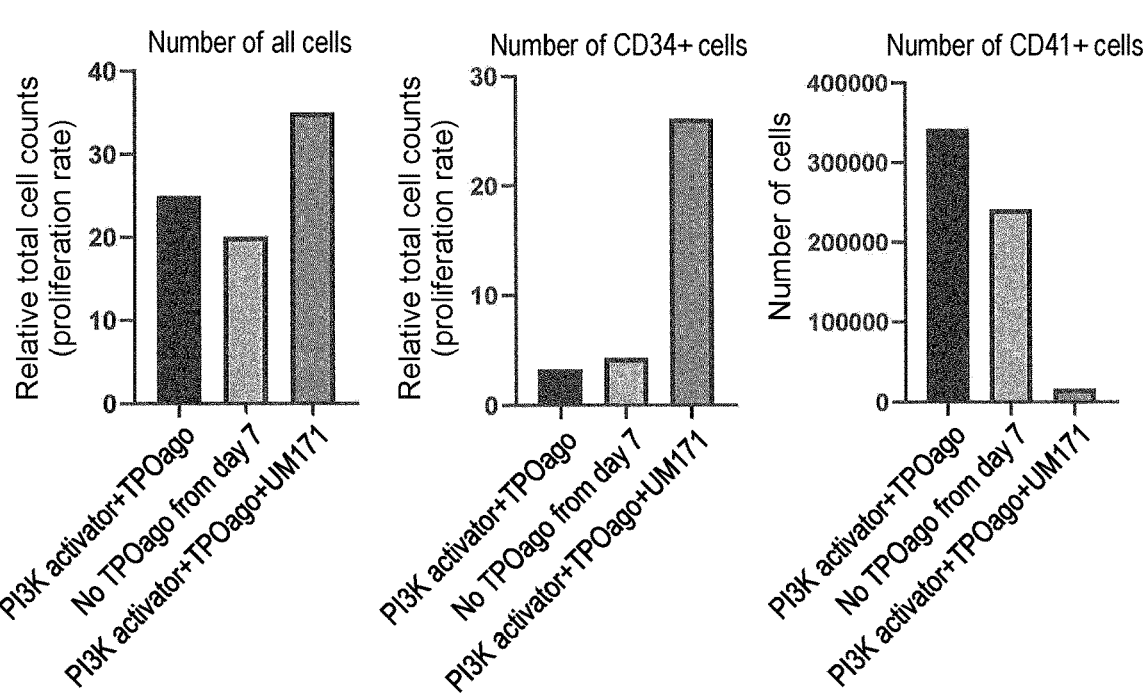
FIG. 14 shows the proliferation rates of total cells and CD34$^+$ cells and the number of CD41$^+$ cells at day 14 when the cells were cultured under Conditions 1 to 3.
Figure 15:
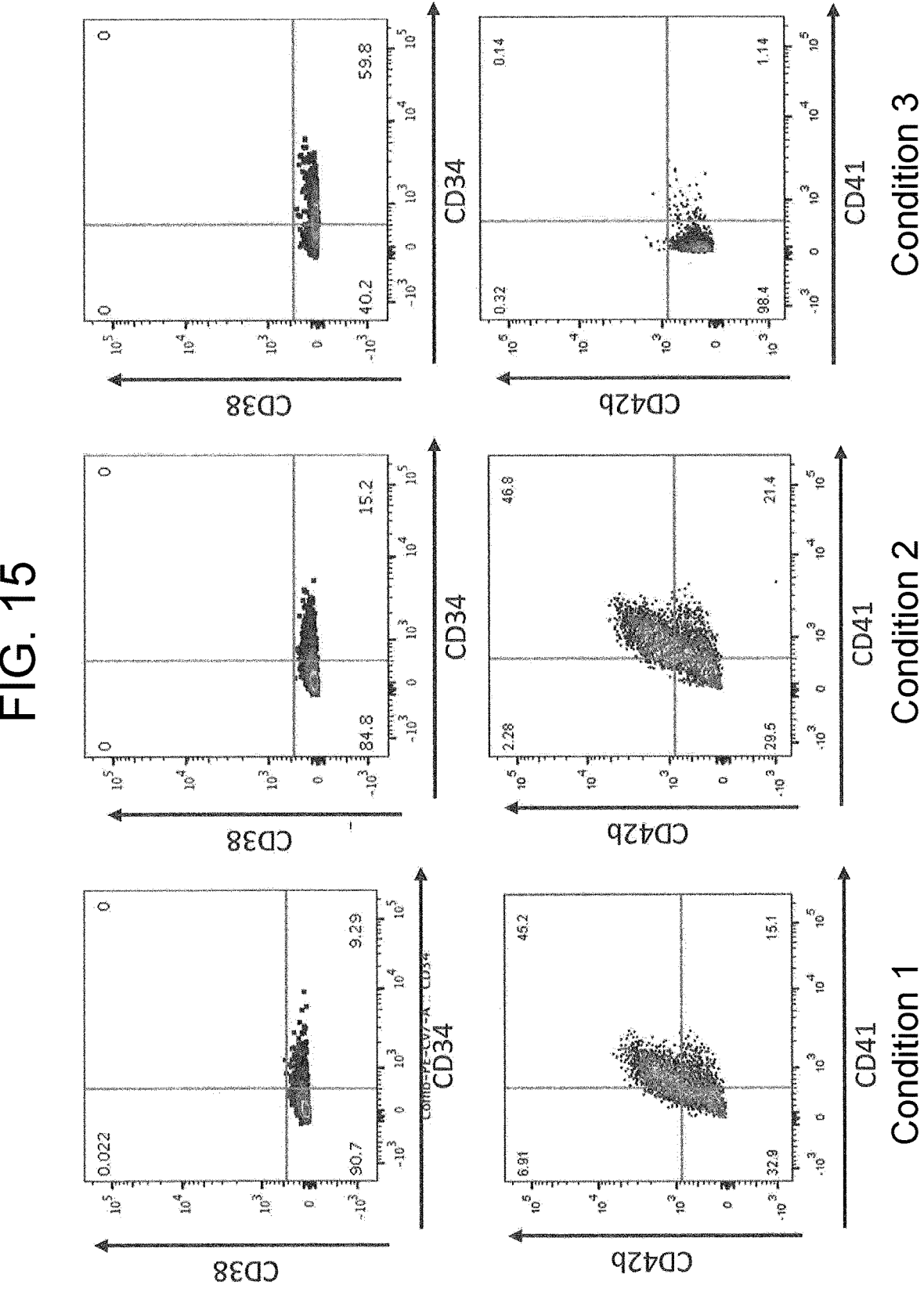
FIG. 15 shows the results of flow cytometry of cells in the culture at day 14 when the cells were cultured under Conditions 1 to 3. The upper panels show the results using CD34 (horizontal axis) and CD38 (vertical axis), and the lower panels show the results using CD41a (horizontal axis) and CD42b (vertical axis).

Further, CD34$^+$ cells were cultured under the following three conditions, and the percentages increase in the number of total cells and the number of CD34$^+$ cells were obtained: Condition 1, cultured in the above-mentioned culture medium for human hematopoietic stem cells which comprised 20 μM PI3Ka and 0.1 μM TPOago instead of SCF and TPO (PI3Ka20 μM+TPOago0.1 μM) for 14 days; Condition 2, cultured in a medium not comprising butyzamide after day 7 (PI3Ka20 μM) (no Buty from day 7); and Condition 3, cultured in a culture medium (PI3Ka20 μM+TPOago0.1 μM) further comprising UM171 (+UM171) for 14 days. Further, the number of CD41$^+$ cells was obtained using a flow cytometer. The results were as shown in FIG. 14. As shown in FIG. 14, under Condition 2, where cells were cultured in a medium from which butyzamide was removed at day 7 after the start of culture, the number of CD34$^+$ cells increased, and the number of CD41$^+$ cells decreased as compared with Condition 1. As shown in FIG. 14, under Condition 3, where cells were cultured in a medium further comprising UM171, the percentage increase of CD34$^+$ cells markedly increased, and the number of CD41$^+$ cells markedly decreased as compared with Conditions 1 and 2. These results revealed that, in the presence of PVA, PI3Ka, and TPOago in a serum-free medium, UM171 proliferated human hematopoietic stem cells and inhibited differentiation of the cells into precursor cells of megakaryocytes or megakaryocytes (see FIG. 15).

Example 5: Experiment of Transplantation of CD34$^+$ Cells after Culture

Figure 16:
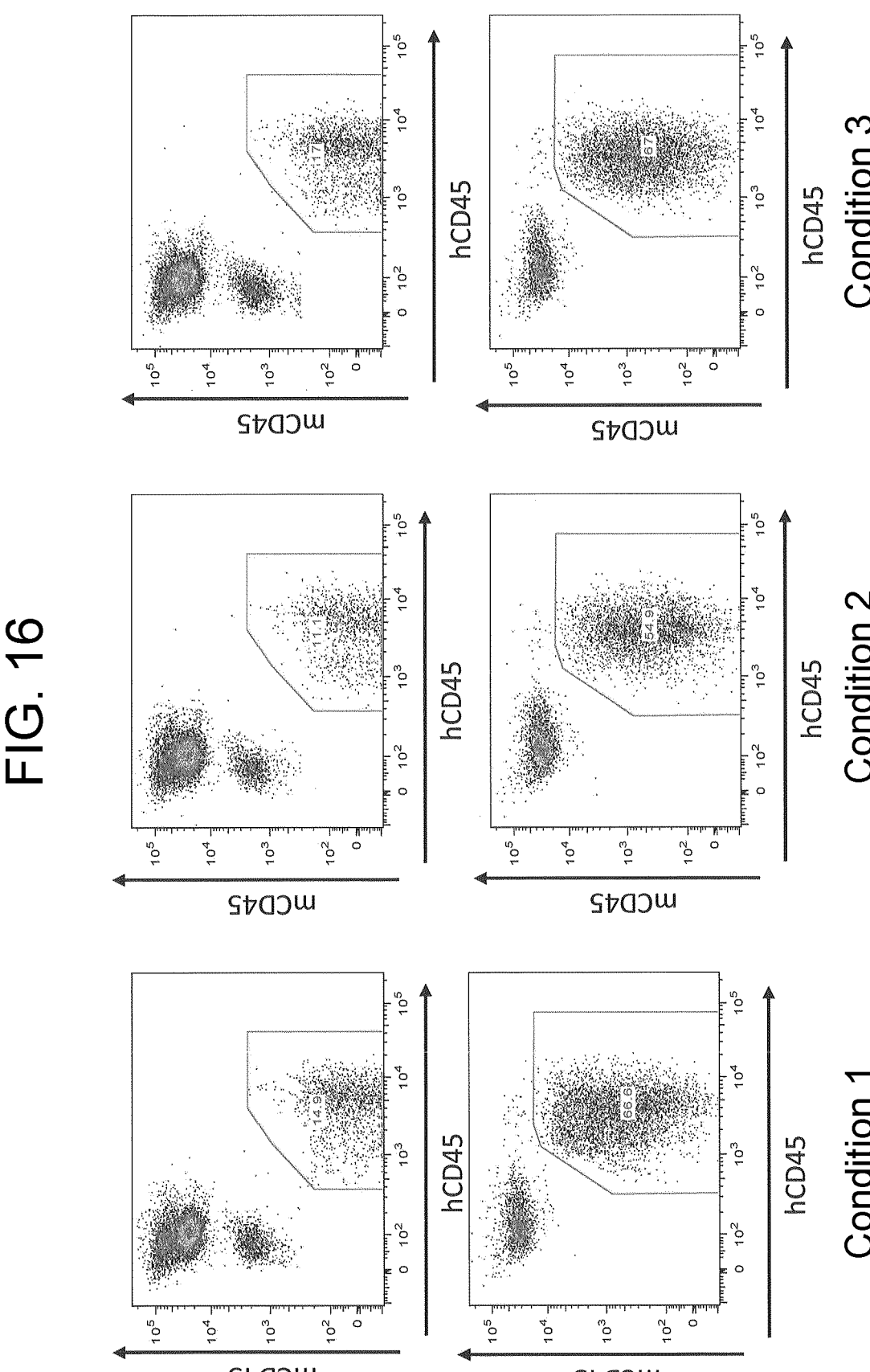
FIG. 16 shows survival of human hematopoietic stem cells in mouse peripheral blood at 12 weeks after culturing human hematopoietic stem cells under Conditions 1 to 3 and transplanting the cells into mice at day 7.

Human CD34$^+$ cells cultured under each of Conditions 1 to 3 for 7 days were transplanted into the irradiated NOG mice, and survival of cells was examined. Specifically, $1 \times 10^4$ human CD34$^+$ cells after culture were transplanted into NOG mice irradiated with 1.5-Gy gamma rays. At 12 weeks after transplantation, peripheral blood was collected from the NOG mice, and cell components in the peripheral blood were analyzed using a flow cytometer. The results were as shown in FIG. 16. As shown in FIG. 16, when CD34$^+$ cells before culture were transplanted, the survival rates of hematopoietic stem cells under Conditions 1 and 2 were 14.9% and 11.1%, respectively, and they increased to 66.6% and 54.9%, respectively, when CD34$^+$ cells after culture were transplanted. Further, while the survival rate of hematopoietic stem cells was 17% when CD34$^+$ cells were transplanted before culture under Condition 3, the survival rate increased to 67% when CD34$^+$ cells after culture were transplanted.

From the above results, it was found that a PI3K activator and a TPO receptor agonist promoted proliferation of human hematopoietic stem cells favorably in the absence of albumin and in the presence of PVA in a serum-free medium, and that proliferated human CD34$^+$ cells maintain the properties of hematopoietic stem cells, improving the survival rate after transplantation into another organism. Further, some human hematopoietic stem cells were differentiated into megakaryocytes when cultured under this condition for a long period of time, enabling acquisition of megakaryocytes, while some human hematopoietic stem cells have tendency to proliferate as CD34$^+$ cells. It was also found that addition of UM171 to the medium could improve the proliferation rate of CD34$^+$ cells and inhibit differentiation into megakaryocytes.

Figure 17:
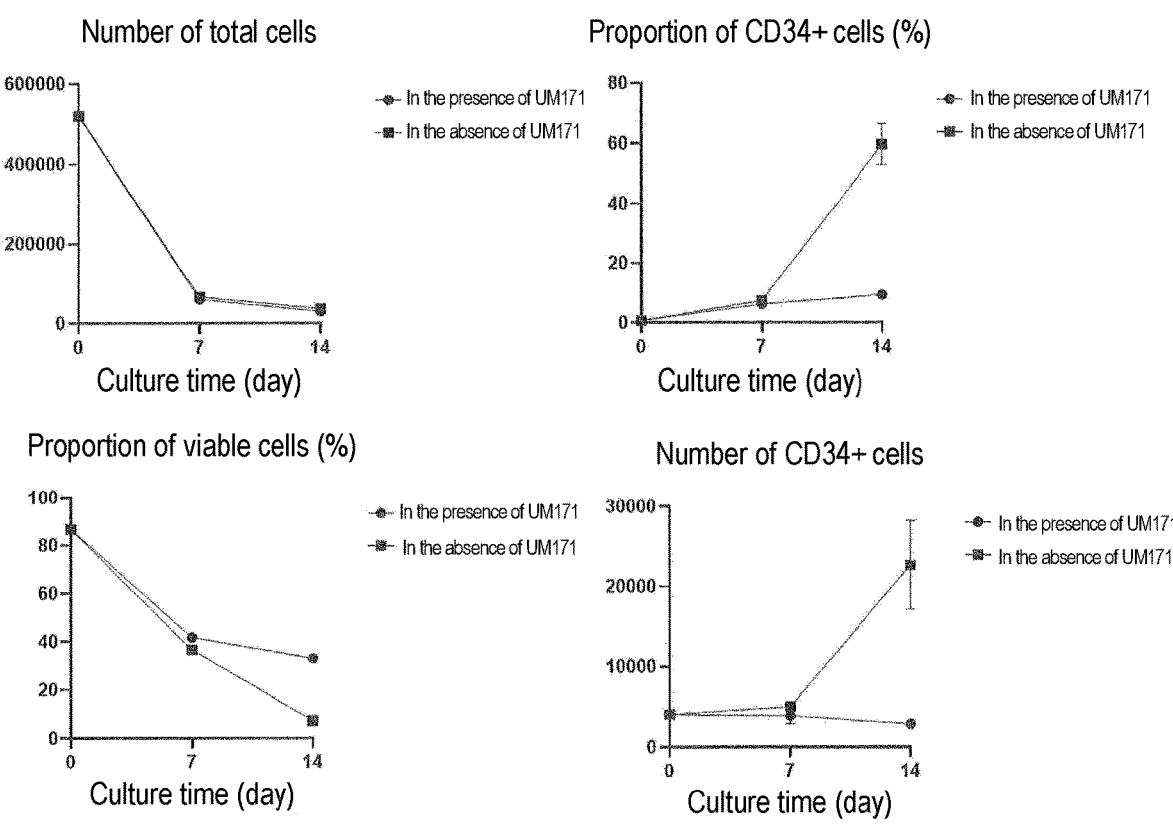
FIG. 17 shows the number of total cells, the proportion of CD34$^+$ cells (%), the proportion of viable cells (%), and the number of CD34$^+$ cells in a culture obtained after isolating mononuclear cells from given umbilical cord blood and culturing the cells in a medium comprising none of albumin, SCF, and TPO but comprising PVA, a PI3K activator, and a TPO receptor agonist under a condition in the presence of or in the absence of UM171 for 14 days.

Subsequently, human mononuclear cells were isolated from fresh human umbilical cord blood. The obtained cells ($5 \times 10^5$ cells) were cultured under Conditions 1 and 3, and the number of total cells, the number of CD34$^+$ cells, the proportion of CD34$^+$ cells in total cells, and the cell survival rate were obtained at days 7 and 14 after the start of culture for the respective conditions. The results were as shown in FIG. 17. As shown in FIG. 17, the number of all mononuclear cells obtained from human umbilical cord blood decreased with time of culture under both conditions. However, the proportion of CD34$^+$ cells in total cells markedly improved under Condition 3 as compared with that under Condition 1. Further, the cell survival rate was also significantly higher under Condition 3 than under Condition 1. Further, while the number of CD34$^+$ cells markedly increased under Condition 3, the number of cells did not increase under Condition 1, although the number of cells was favorably maintained.

The invention claimed is:

1. A method of culturing or manufacturing human hematopoietic stem cells, the method comprising culturing human hematopoietic stem cells in a culture medium, the culture medium comprising polyvinyl alcohol, (1) comprising a phosphatidylinositol 3-kinase (PI3K) activator and one or more selected from the group consisting of thrombopoietin (TPO) and a TPO receptor agonist;

(2) comprising one or more selected from the group consisting of a stem cell factor (SCF) and a PI3K activator, and a TPO receptor agonist; or (3) comprising a PI3K activator and a TPO receptor agonist, wherein the PI3K activator is 740Y-P, wherein the TPO receptor agonist is butyzamide, and wherein the number of human hematopoietic stem cells is increased by the culturing.

2. The method of claim 1, wherein the culture medium is a serum-free medium or chemically defined medium.

3. The method of claim 1, wherein the culture medium comprises substantially no albumin.

4. The method of claim 1, which comprises obtaining an increased amount of human hematopoietic stem cells.

5. The method of claim 1, wherein the culture medium does not comprise SCF.

6. The method according to claim 1, wherein the culture medium comprises 740Y-P and butyzamide.

7. The method of claim 1, wherein the culture medium comprises neither SCF nor TPO.

8. The method of claim 1, wherein the culture medium further comprises 4-N-[2-benzyl-7-(2-methyltetrazol-5-yl)-9H-pyrimido[4,5-b]indol-4-yl]cyclohexane-1,4-diamine (UM171).

9. The method of claim 8, wherein the duration of culture is 7 days or longer.

10. The method of claim 1, wherein the culture medium is a chemically defined medium.

11. The method of claim 1, wherein the culture medium is substantially free from albumin or cytokines.

12. A method of culturing or manufacturing human hematopoietic stem cells, the method comprising culturing human hematopoietic stem cells in a culture medium comprising polyvinyl alcohol as an albumin replacement, (1) a PI3K activator and one or more selected from the group consisting of TPO and a TPO receptor agonist;

(2) one or more selected from the group consisting of SCF and a PI3K activator, and a TPO receptor agonist; or (3) a PI3K activator and a TPO receptor agonist, wherein the PI3K activator is 740Y-P, and wherein the TPO receptor agonist is butyzamide.

13. The method of claim 12, which further comprises 4-N-[2-benzyl-7-(2-methyltetrazol-5-yl)-9H-pyrimido[4,5-b]indol-4-yl]cyclohexane-1,4-diamine (UM171).

* * * * *